United States Patent
Olechno et al.

(10) Patent No.: US 11,237,086 B2
(45) Date of Patent: Feb. 1, 2022

(54) SYSTEM AND METHOD FOR EXTRACTING A TARGET MOIETY FROM A SAMPLE USING ACOUSTIC DROPLET EJECTION

(71) Applicant: Labcyte Inc., San Jose, CA (US)

(72) Inventors: Joseph D. Olechno, San Jose, CA (US); Richard N. Ellson, San Jose, CA (US)

(73) Assignee: LABCYTE, INC., San Jose, CA (US)

( * ) Notice: Subject to any disclaimer, the term of this patent is extended or adjusted under 35 U.S.C. 154(b) by 0 days.

(21) Appl. No.: 17/108,931

(22) Filed: Dec. 1, 2020

(65) Prior Publication Data

US 2021/0088426 A1    Mar. 25, 2021

Related U.S. Application Data

(63) Continuation of application No. 16/292,177, filed on Mar. 4, 2019, now Pat. No. 10,871,430.

(Continued)

(51) Int. Cl.
*G01N 1/00* (2006.01)
*G01N 1/40* (2006.01)
(Continued)

(52) U.S. Cl.
CPC ......... *G01N 1/4055* (2013.01); *B01D 21/283* (2013.01); *B01L 3/0268* (2013.01);
(Continued)

(58) Field of Classification Search
CPC ................. G01N 1/4055; G01N 29/02; G01N 2035/1034; G01N 2001/4061;
(Continued)

(56) References Cited

U.S. PATENT DOCUMENTS 3,616,211 A    10/1971    Pletsch
6,548,308 B2 *    4/2003    Ellson .................. B01J 19/0046
                                                    436/180

(Continued)

OTHER PUBLICATIONS

Sigma-Aldrich, Chemfiles: Enabling Technologies—Ionic Liquids, vol. 5, No. 6 (downloaded from https://www.sigmaaldrich.com/technical-documents/articles/chemfiles/ionic-liquids1.html on Jul. 5, 2017., 24 pages.

(Continued)

*Primary Examiner* — Michael Maskell
(74) *Attorney, Agent, or Firm* — Dianne E. Reed; VLP Law Group, LLP

(57) ABSTRACT

A method and system are provided for extracting a target analyte from a sample using acoustic ejection technology. The method involves applying focused acoustic energy to a fluid reservoir housing a fluid composition that contains a target analyte and comprises an upper region and a lower region, where the concentration of the target analyte in the upper region differs from that in the lower region. The focused acoustic energy is applied in a manner that is effective to result in the ejection of a fluid droplet from the fluid composition into a droplet receiver, wherein the concentration of the analyte in the droplet corresponds to either the concentration of the analyte in the upper region or the concentration of the analyte in the lower region, and wherein the concentration of the analyte is substantially uniform throughout the droplet. The fluid composition may comprise an ionic liquid, used in the extraction of ionic target analytes. Related methods and an acoustic extraction system are also provided.

25 Claims, 4 Drawing Sheets

Related U.S. Application Data

(60) Provisional application No. 62/638,143, filed on Mar. 3, 2018.

(51) Int. Cl.
  *B01D 21/28*   (2006.01)
  *B01L 3/02*    (2006.01)
  *B01L 3/00*    (2006.01)
  *C12N 15/10*   (2006.01)
  *G01N 29/02*   (2006.01)
  *H01J 49/00*   (2006.01)
  *H01J 49/04*   (2006.01)
  *G01N 35/10*   (2006.01)

(52) U.S. Cl.
  CPC ...... *B01L 3/50857* (2013.01); *C12N 15/1003* (2013.01); *G01N 29/02* (2013.01); *H01J 49/0031* (2013.01); *H01J 49/0431* (2013.01); *B01L 2200/143* (2013.01); *B01L 2300/16* (2013.01); *B01L 2400/02* (2013.01); *B01L 2400/0436* (2013.01); *G01N 2001/4061* (2013.01); *G01N 2035/1034* (2013.01)

(58) Field of Classification Search
  CPC . B01D 21/283; B01L 3/0268; B01L 3/50857; B01L 2200/143; B01L 2300/16; B01L 2400/02; B01L 2400/0436; C12N 15/1003; H01J 49/0031; H01J 49/0431
  USPC .......................................... 250/281, 282, 288
  See application file for complete search history.

(56) References Cited

U.S. PATENT DOCUMENTS

| | | | |
|---|---|---|---|
| 6,642,061 B2* | 11/2003 | Ellson | B01J 13/04 436/180 |
| 6,893,115 B2 | 5/2005 | Hadimioglu et al. | |
| 6,932,097 B2 | 8/2005 | Ellson | |
| 6,938,995 B2 | 9/2005 | Mutz et al. | |
| 7,354,141 B2 | 4/2008 | Ellson et al. | |
| 7,405,395 B2 | 7/2008 | Ellson et al. | |
| 7,481,511 B2 | 1/2009 | Mutz et al. | |
| 7,717,544 B2 | 5/2010 | Stearns et al. | |
| 7,784,331 B2 | 8/2010 | Ellson et al. | |
| 7,899,645 B2 | 3/2011 | Qureshi | |
| 7,900,505 B2 | 3/2011 | Mutz | |
| 8,107,319 B2 | 1/2012 | Stearns et al. | |
| 8,453,507 B2 | 6/2013 | Ellson et al. | |
| 8,503,266 B1 | 8/2013 | Stearns et al. | |
| 8,544,976 B2 | 10/2013 | Ellson | |
| 8,770,691 B2 | 7/2014 | Stearns et al. | |
| 8,882,226 B2 | 11/2014 | Ellson | |
| 9,458,190 B2 | 10/2016 | Lazarev et al. | |
| 9,460,904 B1 | 10/2016 | Greving et al. | |
| 2002/0155231 A1 | 10/2002 | Ellson et al. | |
| 2009/0289213 A1 | 11/2009 | Hsieh | |
| 2012/0085645 A1 | 4/2012 | Mousa et al. | |
| 2018/0104694 A1 | 4/2018 | Huff et al. | |

OTHER PUBLICATIONS

Branco, Luis C., et al., "Physico-Chemical Properties of Task-Specific Ionic Liquids", Ionic Liquids: Theory, Properties, New Approaches (Intech), Feb. 28, 2011, pp. 61-94.
Chandran, Aneesh, et al., "Groove binding mechanism of ionic liquids: a key factor in long-term stability of DNA in hydrated ionic liquids?", Journal of the American Chemical Society 134.50, 2012, pp. 20330-20339.
Clark, Kevin D., et al., "Extraction of DNA by Magnetic Ionic Liquids: Tunable Solvents for Rapid and Selective DNA Analysis", Anal. Chem. vol. 87, 2015, 1552-1559.
Clark, Kevin David, et al., "Maximizing ion-tagged oligonucleotide loading on magnetic ionic liquid supports for the sequence-specific extraction of nucleic acids", Analytical Chemistry 91.9, 2019, pp. 1-25.
Forbes, Monica M., et al., "Examination of Inertial Cavitation of Optison™ in Producing Sonoporation of Chinese Hamster Ovary Cells", Ultrasound Med Biol. 34(12), Dec. 2018, pp. 1-22.
Forbes, Monica M., et al., "Frequency-Dependent Evaluation of the Role of Definity in Producing Sonoporation of Chinese Hamster Ovary Cells", American Institute of Ultrasound in Medicine, J Ultrasound Med 30, 2011, pp. 61-69.
Forbes, Monica Mary, "The Role of Ultrasound Contrast Agents in Producing Sonoporation", Thesis PhD, Department of Bioengineering, University of Illinois at Urbana-Champaign, 2009, 2009, 166 pages.
Freire, Mara G., et al., "An overview of the mutual solubilities of water-imidazolium-based ionic liquids systems", Fluid Phase Equilibria 261.1-2, 2007, pp. 449-454.
Fuchs-Telka, Sabine, et al., "Hydrophobic ionic liquids for quantitative bacterial cell lysis with subsequent DNA quantification", Analytical and Bioanalytical Chemistry 409.6, Dec. 21, 2016, pp. 1503-1511.
Garcia, Eric Gonzalez, et al., "Direct extraction of genomic DNA from maize with aqueous ionic liquid buffer systems for applications in genetically modified organisms analysis", Analytical and Bioanalytical Chemistry 406.30, Nov. 9, 2014, pp. 7773-7784.
Jumbri, K., et al., "An insight into structure and stability of DNA in ionic liquids from molecular dynamics simulation and experimental studies", Royal Society of Chemistry, Physical Chemistry Chemical Physics 16.27, 2013, pp. 1-11.
Kirby, K. S., "A New Method for the Isolation of Ribonucleic Acids from Mammalian Tissues", Polyol Dehydrogenases, 64(3), Apr. 12, 1956, pp. 405-408.
Li, Tianhao , "Engineering of Novel Task-specific Ionic Liquids for the Selective Extraction and Preconcentration of DNA and Emerging Contaminants", Dissertation, Submitted to the Graduate Faculty as partial fulfillment of the requirements for the Doctor of Philosophy Degree in Chemistry, University of Toledo, Dec. 2013, 181 pages.
Li, Tianhao, et al., "Ionic liquids as solvents for in situ dispersive liquid-liquid microextraction of DNA", Journal of Chromatography A 1272, 2013, pp. 8-14.
Liu, Mei, et al., "Extraction of DNA from complex biological sample matrices using guanidinium ionic liquid modified magnetic nanocomposites", Royal Society of Chemistry, RSC Advances 9.40, 2019, pp. 23119-23128.
Nacham, Omprakash , et al., "Extraction and purification of DNA from complex biological sample matrices using solid-phase microextraction coupled with real-time PCR", Analytical Chemistry 88.15, 2016, pp. 7813-7820.
Pabbathi, Ashok , et al., "Spectroscopic and molecular docking study of the interaction of DNA with a morpholinium ionic liquid", The Journal of Physical Chemistry 8 119.34, American Chemical Society, 2015, pp. 11099-11105.
Plechkova, Natalia V., et al., "Applications of Ionic Liquids in the Chemical Industry", Chem. Soc. Rev. 37, Nov. 30, 2007, pp. 123-150.
Rutkowska, Malgorzata, et al., "Application of Additional Factors Supporting the Microextraction Process", TrAC Trends in Analytical Chemistry 97(14), Dec. 2017, pp. 104-119.
Sharma, Mukesh , et al., "High concentration DNA solubility in bio-ionic liquids with long-lasting chemical and structural stability at room temperatur", RSC Advances 5.51, 2015, pp. 1-5.
Sinclair, Ian , et al., "Novel Acoustic Loading of a Mass Spectrometer: Toward Next-Generation High-Throughput MS Screening", J. Laboratory Automation 21(1), 2016, pp. 19-26.
Tan, Siun Chee, et al., "DNA, RNA, and Protein Extraction: The Past and the Present", J. Biomed. Biotech vol. 2009, 2009, 10 pages.
Tateishi-Karimata, Hisae , et al., "Comparable Stability of Hoogsteen and Watson-Crick Base Pairs in Ionic Liquid Choline Dihydrogen Phosphate", Scientific Reports 4, Jan. 8, 2014, pp. 1-7.

(56) References Cited

OTHER PUBLICATIONS

Tateishi-Karimata, Hisae, et al., "Structure, stability and behaviour of nucleic acids in ionic liquids", Nucleic acids research vol. 42, No. 14, Jul. 10, 2014, pp. 8831-8844.
Vijayaraghavan, Ranganathan, et al., "Long-term structural and chemical stability of DNA in hydrated ionic liquids", Angewandte Chemie International Edition 49.9, 2010, pp. 1631-1633.
Wang, Jian-Hua, et al., "Direct Extraction of Double-Stranded DNA into Ionic Liquid 1-Butyl-3-methylimidazolium Hexafluorophosphate and Its Quantification", Anal. Chem. vol. 79, Jan. 2, 2007, pp. 620-625.
Nang, Xiaofeng, et al., "Novel Polymeric Ionic Liquid Microspheres with High Exchange Capacity for Fast Extraction of Plasmid DNA", Anal. Chim. Acta 837, Jun. 5, 2014, pp. 64-69.
Yao, Cong, et al., "Dispersive liquid-liquid microextraction using an in situ metathesis reaction to form an ionic liquid extraction phase for the preconcentration of aromatic compounds from water", Analytical and Bioanalytical Chemistry 395.5, Sep. 1, 2009, pp. 1491-1502.

* cited by examiner

Ejection of DNA pulled from ionic liquid in a dual LLE:

SYSTEM AND METHOD FOR EXTRACTING A TARGET MOIETY FROM A SAMPLE USING ACOUSTIC DROPLET EJECTION

CROSS-REFERENCE TO RELATED APPLICATION

This is a continuation of U.S. Ser. No. 16/292,177, filed Mar. 4, 2019, which claims priority under 35 U.S.C. § 119(e)(1) to provisional U.S. Patent Application Ser. No. 62/638,143, filed Mar. 3, 2018, the disclosures of which are incorporated by reference herein.

BACKGROUND OF THE INVENTION

(1) Technical Field

The present invention relates generally to systems and methods for extracting a target analyte from a fluid composition using acoustic droplet ejection. The invention finds utility in numerous fields, including chemistry and biology.

(2) Description of Related Art

The extraction of molecules from a mixture is an essential step in processes employed in numerous technical areas, including synthetic organic chemistry, materials science, pharmaceutical research and development, and molecular biology. Although now required in many contexts, the extraction of biomolecules such as nucleic acids and proteins is particularly challenging insofar as they are normally contained within complex host environments such as cells, tissues, and blood. Efficient and effective extraction of DNA, RNA, and proteins is nevertheless necessary in numerous processes and products. Diagnostic kits, identity and relationship testing, pathogen detection, tissue typing, and genetic research are just several examples.

Purification of DNA can involve the separation and removal of chromosomal and/or mitochondrial DNA from a biological environment, or it may be carried out in the context of isolating recombinant DNA constructs, i.e., DNA containing a recombinant sequence, such as a plasmid. Polymerase chain reaction (PCR) amplification of DNA, diagnostic testing procedures, and a host of sensitive assays require a high degree of purity. Contaminants in a DNA sample can inhibit one or more critical steps of a diagnostic or analytical procedure. Some contaminants, for example, can inhibit the polymerase chain reaction or the action of restriction enzymes.

Any DNA purification method requires (1) effective disruption of a biological host environment, e.g., cells or tissues, that contains the target DNA; (2) denaturation of proteins and nucleoprotein complexes using a protease and/or denaturant; (3) inactivation of endogenous nucleases; and (4) removal of the target DNA from the sample. The isolated target DNA should be free of any compounds or materials originally present, e.g., proteins, lipids, RNA, other nucleic acids, and the like, and in most cases the purification process must avoid DNA fragmentation resulting from mechanical shearing or the presence of contaminants. Isolation of RNA is even more complicated, insofar as RNA is inherently unstable, strong denaturants are necessary to inhibit endogenous RNAses, RNAses are heat-stable and refold following thermal denaturation, and the RNAses, lacking cofactors, are difficult to inactivate.

In nucleic acid purification, disruption of cells or tissues is usually carried out using a detergent to disrupt the lipid bilayer of the cell membrane. Detergents disrupt both lipid-lipid and lipid-protein interactions in the cell membrane, enabling solubilization of membrane components. With organisms that contain cell walls in addition to a cell membrane, additional treatment may be required; for instance, treatment with lysozyme is necessary to digest the peptidoglycan cell wall of gram-positive bacteria and treatment with lyticase or zymolase is required to disrupt the polysaccharide cell wall of yeasts.

Denaturation of proteins and nucleoproteins involves modification of protein conformation by disruption of secondary structure, and is carried out using protein denaturing agents such as ionic detergents, chaotropic agents, reducing agents, heat, and/or proteases. In mammalian cells, DNA is compacted with histones in a macromolecular nucleoprotein structure (i.e., chromatin), and denaturation enables release of chromosomal DNA from the nucleoprotein complex. Chelating agents such as ethylenediaminetetraacetic acid (EDTA) are typically used to inactivate nucleases, as is Proteinase K. Some commercial systems require stepwise processing, i.e., cell lysis, denaturation, and nuclease inactivation, and other systems provide a single solution containing components for carrying out all three of the aforementioned steps.

Ultimately, the target DNA must be isolated from the treated biological sample, which will likely contain proteins, protein fragments, lipids, carbohydrates, salts, and cell debris. Historically, DNA was purified via liquid-liquid extraction. The aqueous cell hydrolysate was shaken with a phenol-chloroform mixture, optionally containing some isoamyl alcohol to inhibit RNAse activity. This mixture separates into two layers with the hydrophobic chloroform-phenol lower phase containing the proteins, lipids, carbohydrates, and cell debris, while nucleic acids remain in the upper aqueous phase. The aqueous DNA solution of the upper phase is collected, the DNA is precipitated from the supernatant, and the DNA precipitate is rinsed and dissolved with buffer. The technique is cumbersome and time-consuming, however, and, as has been widely noted, chloroform is highly toxic and phenol is flammable, corrosive, and toxic as well.

Liquid-liquid extraction has been largely replaced with a solid-phase nucleic acid purification method using centrifuge-based columns. In this case, the cell lysate is mixed with a buffer solution and either a chaotropic agent or a short-chain alcohol. The lysate is transferred to a column and centrifuged to drive the liquid through the solid phase, which has been surface treated to retain the negatively charged nucleic acid. Proteins and other contaminants are washed through the column while nucleic acids bind to it. After washing steps, the nucleic acids are eluted with water or buffer (e.g., dilute TRIS-EDTA buffer at a pH of about 8.4). Mixed-bed solid phase extraction has also been disclosed; see U.S. Pat. No. 6,376,194 to Smith et al. While easier and safer than conventional liquid-liquid extraction employing the phenol-chloroform technique, column-based DNA extraction still requires manual intervention and is not easily automated.

In a variation on traditional solid phase separation, a magnetic bead-based nucleic acid purification method has been developed. In this process, magnetic beads having coated or otherwise treated surfaces bind nucleic acids in the presence of a chaotropic agent. The beads are combined with a biological sample, and nucleic acid in the sample binds to the bead surface. A magnet is used to pull the beads with surface-bound nucleic acid to a stable position in a microplate well, centrifuge tube, or other vessel. Once the beads are magnetically immobilized, the supernatant containing the impurities is removed, the beads are washed with clean wash buffer, and the nucleic acids are displaced from the magnetic beads with a small volume of dilute elution buffer. By eliminating centrifugation, the technique is generally more amenable to automation and higher throughput than other solid phase purification methods. However, the cost to clean up each sample is substantial Various types of extraction techniques for isolating and purifying DNA, RNA, and proteins are described in Tan et al. (2009) J. Biomed. Biotech., Article ID 574398. As explained therein, there is an ongoing need for improved ways to isolate and purify biomolecules. Tan et al. note that automation of extraction procedures is desirable in order to reduce working time, decrease labor costs, enhance worker safety, and, ideally, increase both the reproducibility and the quality of results. Tan et al. further note that commercially available automated systems are somewhat limited insofar as they tend to be large, expensive, and complex, intended for use in medium to large laboratories, while more recent automation processes adapted for small and medium sample throughput still require a time-consuming extraction process, on the order of 20 to 40 minutes of processing time per sample. Proper liquid handling is essential, both for each extraction step of an automated procedure and for transferring liquids as necessary; optimally, as explained by Tan et al., robotic workstations should be fully automated and thereby obviate the need for pre-processing steps. Tan et al. additionally point out that continued improvement in miniaturization is necessary, and would remedy a weakness of available extraction systems.

Acoustic droplet ejection (ADE) is a methodology that has been disclosed as useful in the ejection of immiscible fluids; see U.S. Pat. Nos. 6,548,308 and 6,642,061 to Ellson et al. The aforementioned patents describe the use of ADE to eject droplets from immiscible liquids onto a substrate surface, where the droplets generally have a first region corresponding to one of the liquids and a second region corresponding to the other liquid. ADE has not been implemented in the extraction of target moieties from a sample, however, and it is well known that development of extraction techniques can be complicated and problematic, as explained by Tan et al., supra.

An ideal extraction system and method would accomplish at least the following goals:

Provide the isolated target molecule in high purity;

Be capable of use to extract any of a wide variety of target molecules;

Yield accurate, consistent, and reproducible results;

Be fully automated;

Be capable of use under standard laboratory conditions without need for high temperatures or an inert atmosphere;

Minimize per-sample processing time and enable high-throughput sample processing;

Allow effective and efficient processing of very small sample sizes, on the order of nanoliters or smaller; accuracy and reliability;

Eliminate the need for toxic, volatile solvents;

Rely on reagents that can be recycled and reused in a subsequent extraction step; and Enable rapid introduction of the extracted target moiety into analytical device such as a mass spectrometer.

SUMMARY OF THE INVENTION

The invention is addressed to the above-mentioned needs in the art and provides a method and system for extracting a target analyte using acoustic droplet ejection (ADE) technology. The target analyte is in a fluid composition, e.g., dissolved in a solvent or solvent mixture, and may comprise a single analyte or a mixture of analytes in a multi-component composition. The fluid composition may comprise a biological sample such as living tissue, cells, blood, or the like, which may or may not have been processed in some manner prior to extraction. The invention employs ADE technology and, in a preferred embodiment, liquid-liquid partitioning, making use of liquids that, for example, have different affinities for various types of components in a sample, and/or liquids in which the solubility of a component of interest is different. The method and system of the invention can be readily implemented in the high-throughput context and are useful in extracting a variety of target molecules from samples, including small volumes of biological samples composed of complex biological mixtures.

The present extraction method encompasses the partial or complete removal of a target analyte from an initial fluid composition, and also encompasses a separation process in which a final fluid composition contains a non-target component at a lower concentration than in the initial fluid composition.

In a first embodiment of the invention, a method is provided for producing a fluid droplet containing a target analyte at a selected concentration. The method comprises: (a) providing, in a fluid reservoir, a fluid composition that contains the target analyte and comprises an upper region and a lower region, wherein the analyte is at a first concentration in the upper region and at a second concentration in the lower region, and further wherein the second concentration is different from the first concentration; and (b) applying focused acoustic energy to the fluid reservoir in a manner effective to eject a fluid droplet from the fluid composition into a droplet receiver, wherein the ejected droplet comprises the target analyte at the selected concentration, and further wherein the selected concentration is (i) substantially equivalent to either the first concentration or the second concentration, and (ii) substantially uniform throughout the droplet. The fluid composition in the fluid reservoir generally comprises a sample that contains the target analyte, e.g., a biological sample. The biological sample may comprise a sample dissolved or suspended in a fluid or the biological sample may itself be fluidic.

In one aspect of the aforementioned embodiment, the upper region of the fluid composition comprises an upper layer of a first liquid, while the lower region of the fluid composition comprises a lower layer of a second liquid. Depending on the target analyte, the first liquid, and the second liquid, the analyte may partition into the first liquid or the second liquid preferentially. That is, the first and second liquids are selected such that the first liquid has a first affinity for the target analyte and the second liquid has a second affinity for the target analyte, and the first affinity and the second affinity are different. For example, with a hydrophilic, e.g., ionic, target analyte, a hydrophilic upper liquid, and a hydrophobic lower liquid, the target analyte will tend to partition into the upper, hydrophilic liquid. As another example, when the solubility of the target analyte is greater in the lower liquid than in the upper liquid, the target analyte will tend to partition into the lower liquid. The first liquid and the second liquid may differ in volatility, density, viscosity, and/or other physical or chemical characteristics.

In a related aspect, the solubility of the target analyte in the lower liquid differs from its solubility in the upper liquid by at least about 50%.

In another related aspect, the solubility of the target analyte in the lower liquid differs from its solubility in the upper liquid by at least about 85%.

In another aspect of the aforementioned embodiment, the target analyte is an ionic target analyte, i.e., an analyte that is ionized at a selected pH, e.g., a pH in the range of about 6 to about 8. An ionic target analyte may be a negatively charged moiety or a positively charged moiety, in association with a cationic or anionic counterion, respectively.

In another aspect, the target analyte comprises a biomolecule. The biomolecule may be a nucleic acid, a peptide or protein, a lipidic moiety, or the like. In a related aspect, the biomolecule comprises DNA. Peptides, proteins, and the like may have a molecular weight in the range of about 100 daltons to about 200 kilodaltons. Much larger target analytes are envisioned, however, insofar as the present invention is useful in conjunction with large nucleic acid fragments, unfragmented single-stranded or double-stranded DNA, an entire genome or more than one entire genome, and intact cells.

In a further aspect, the fluid composition comprises an ionic liquid, i.e., a salt that is in the form of a liquid at the conditions used for extraction.

In a related aspect, the method employs an ionic liquid in the acoustic ejection of a charged biomolecule, such as a nucleic acid (e.g., DNA) from a fluid composition.

In another related aspect, the ionic liquid serves as a first liquid, and an aqueous liquid serves as a second liquid, where the aqueous liquid is buffered to a pH that alters the relative affinity of the ionic analyte for the ionic liquid and the aqueous liquid.

In another aspect of the aforementioned embodiment, the method further includes, prior to step (a): subjecting a combination of the sample and a miscible mixture of the first liquid and the second liquid to a condition that renders the two liquids substantially immiscible, resulting in the partitioning of the fluid composition into the upper region and the lower region.

In another aspect of the embodiment, the droplet receiver comprises an analytical instrument. In a related aspect, the analytical instrument is a mass spectrometer.

In another aspect of the embodiment, step (b) of the method is repeated multiple times to eject multiple fluid droplets into the droplet receiver.

In another aspect of the embodiment, the droplet receiver comprises a droplet receiving reservoir. In a related aspect, step (b) of the method is repeated multiple times until at least 20 wt. % of the target analyte is transferred from the fluid reservoir to the droplet receiving reservoir.

In a further aspect of the embodiment, the fluid reservoir is one of a plurality of reservoirs each housing a fluid composition containing a target analyte, wherein any two of the fluid compositions may be the same or different, and/or any two of the target analytes may be the same or different. The plurality of reservoirs may be arranged in an array and/or contained within a substrate that comprises an integrated multiple reservoir unit. In a related aspect, fluid droplets are acoustically ejected from an array of fluid reservoirs into a corresponding array of droplet receiving reservoirs.

In another aspect of the embodiment, the fluid composition in the fluid reservoir has a volume of no more than about 125 µL.

In another aspect of the embodiment, the ejected fluid droplet has a volume of no more than about 60 nL.

In another aspect of the embodiment, the fluid droplet has a volume of no more than about 30 nL.

In a related aspect of this embodiment, acoustic droplet ejection is carried out with respect to a plurality of fluid reservoirs in succession, with rapid reservoir-to-reservoir transitions, e.g., at most about 0.5 seconds, or at most about 0.1 seconds, or at most about 0.001 seconds.

In a further aspect of the embodiment, the interior surfaces of the fluid reservoir are coated with a surface coating composition. In a related aspect, the surface coating is selected to repel or attract the upper fluid layer, thereby altering the shape of the meniscus and the thickness of the central region of the upper fluid layer.

In another aspect of the embodiment, the method further includes detecting the presence of a liquid-liquid boundary between the upper and lower fluid layers. In a related aspect, fluid droplets are repeatedly ejected from the upper fluid layer until no liquid-liquid boundary is detected, meaning that substantially all of the upper layer has been removed from the fluid composition and the acoustic ejection process can be stopped.

In another embodiment of the invention, a method is provided for extracting an ionic target analyte from a sample, where the method comprises admixing the sample with an ionic liquid and a non-ionic liquid under conditions that facilitate partitioning of the ionic analyte into the ionic liquid, and acoustically removing the non-ionic liquid from the mixture.

In an additional embodiment of the invention, a method is provided for extracting an ionic target analyte from a sample, where the method comprises admixing the sample with an ionic liquid and a non-ionic liquid under conditions that facilitate partitioning of the ionic analyte into the ionic liquid to provide a solution of the ionic analyte in the ionic liquid, removing the non-ionic liquid from the mixture, and acoustically ejecting droplets of the ionic analyte solution into a droplet receiver.

In another embodiment, the invention provides an extraction method that comprises: (a) providing, in a fluid reservoir, an initial fluid composition that contains the target analyte and comprises an upper layer of a first liquid and a lower layer of a second liquid, wherein the analyte is at a first concentration in the upper layer and at a second concentration in the lower layer, wherein the second concentration is higher than the first concentration; and (b) repeatedly applying focused acoustic energy to the fluid reservoir in a manner effective to eject fluid droplets of the upper layer of the fluid, thereby removing at least a portion of the upper layer while allowing the lower layer to remain in the fluid reservoir.

In a further embodiment of the invention, a method is provided for extracting an ionic analyte from a biological sample, comprising: (a) acoustically ejecting droplets of a biological sample comprising the ionic analyte and an aqueous medium into an ionic liquid contained in a droplet receiving reservoir; (b) inverting the droplet receiving reservoir, whereby an upper aqueous layer and a lower ionic liquid layer comprising ionic analyte are formed; and (c) removing the upper aqueous layer to provide an ionic analyte solution comprising the ionic analyte in the ionic liquid. The biological sample may be a processed biological sample, e.g., a sample containing lysed cells.

In one aspect of the embodiment, the aqueous medium comprises a buffer system that maintains the biological sample at a first pH, wherein the first pH is selected so that at least 60 wt. % of the ionic analyte in the biological sample partitions into the ionic liquid upon admixture therewith.

In another aspect of the embodiment, the method further comprises, after step (c), step (d): admixing the ionic analyte solution with an extraction buffer having a second pH selected so that at least 60 wt. % of the ionic analyte in the ionic liquid partitions into the extraction buffer.

In an additional embodiment, the invention provides a method for acoustically extracting DNA from an aqueous biological sample, where the method comprises:

(a) admixing the aqueous biological sample with an ionic liquid in a fluid reservoir under conditions effective to provide a fluid composition that comprises an upper aqueous layer and a lower ionic liquid layer;

(b) treating the fluid composition so that DNA in the biological sample partitions into the lower ionic liquid layer;

(c) removing the upper aqueous layer so that a DNA solution in the ionic liquid remains in the fluid container;

(d) admixing the DNA solution with an extraction buffer having a pH selected so that at least 60 wt. % of the DNA in the ionic liquid partitions into the extraction buffer; and (e) successively acoustically ejecting droplets of the DNA-containing extraction buffer into a droplet receiver.

In another embodiment, the invention provides a method for extracting lipidic components from an aqueous biological sample, comprising: admixing the aqueous biological sample with an organic solvent in a fluid reservoir, thereby providing a partitioned fluid composition with an upper organic layer comprising a lipid solution and a lower aqueous layer; and successively acoustically ejecting droplets of the lipid solution into a droplet receiver.

In a further embodiment of the invention, an acoustic extraction system is provided for extracting an ionic target analyte from a sample, comprising: (a) a fluid reservoir housing a fluid composition comprising the ionic target analyte and an ionic liquid; and (b) an acoustic droplet ejector in acoustic coupling relationship with the fluid reservoir for generating acoustic radiation in a manner effective to eject a fluid droplet from the fluid composition into a droplet receiver, the ejector comprising an acoustic radiation generator and a focusing means for focusing the acoustic radiation at a focal point within the reservoir.

In one aspect of this embodiment, the system further includes the droplet receiver, e.g., an analytical instrument such as a mass spectrometer or the like, or a droplet receiving reservoir.

In another aspect of this embodiment, the system comprises a plurality of fluid reservoirs each housing a fluid composition comprising the ionic target analyte and an ionic liquid, wherein any two of the fluid compositions may be the same or different, and/or any two of the target analytes may be the same or different. The plurality of reservoirs may be arranged in an array and/or contained within a substrate that comprises an integrated multiple reservoir unit. In a related aspect of the embodiment, the system further includes a means for positioning the ejector in acoustic coupling relationship with respect to each of the fluid reservoirs in succession.

In a related aspect of the embodiment, the target analyte comprises a biomolecule.

In another embodiment, a method is provided for synthesizing and acoustically extracting a reaction product from a reaction mixture. The method comprises:

(a) providing, in a fluid reservoir, a reaction mixture containing a first reactant, a second reactant, and a fluid medium, where the reaction mixture typically has a volume in the range of about 1 nL to about 3 mL;

(b) subjecting the reaction mixture to a reaction condition that causes a chemical reaction between the first reactant and the second reactant to give a reaction product, where the fluid medium comprises a first liquid in which the reaction product has a first solubility;

(c) mixing into the reaction mixture a second liquid that is substantially immiscible with the first liquid and in which the reaction product has a second solubility that differs from the first solubility by at least 50%, thereby providing a fluid composition having an upper layer and a lower layer containing different concentrations of the reaction product; and (d) applying focused acoustic energy to the fluid reservoir in a manner effective to eject a fluid droplet containing the reaction product into a droplet receiver.

In a related aspect of the aforementioned embodiment, the reaction mixture further includes a reaction catalyst. In another related aspect, the method results in the partitioning of the reaction product and the catalyst into different liquids, thereby substantially separating the reaction product and the catalyst.

In another related aspect of the aforementioned embodiment, the reaction mixture further includes a surfactant. In another related aspect, the method results in the partitioning of the reaction product and the surfactant into different liquids, thereby substantially separating the reaction product and the surfactant.

In a further embodiment, the invention provides a method for the synthesis and acoustic transfer of a reaction product, the method comprising:

(a) providing, in a fluid reservoir, a reaction mixture comprised of a first reactant, a second reactant, and a fluid medium, the reaction mixture typically having a volume in the range of about 1 nL to about 3 mL;

(b) subjecting the reaction mixture to a reaction condition that causes a chemical reaction between the first reactant with the second reactant to give a reaction product; and (c) applying focused acoustic energy to the fluid reservoir in a manner effective to eject a fluid droplet containing the reaction product into a droplet receiver.

The invention additionally provides, in another embodiment, a method for determining a distribution coefficient D of an analyte in a mixture of two solvents, wherein the method comprises:

(a) combining, in a fluid reservoir, a known quantity X of an analyte with a first volume $V_1$ of a first solvent and a second volume $V_2$ of a second solvent that is substantially immiscible with the first solvent, such that the analyte has a concentration $X/(V_1+V_2)$ in the first solvent and the second solvent combined, thereby forming a two-phase fluid composition having an upper layer of the first solvent and a lower layer of the second solvent, wherein the analyte has a concentration $C_1$ in the first solvent and a concentration $C_2$ in the second solvent;

(b) acoustically ejecting a droplet of the upper layer;

(c) determining $C_1$ in the ejected droplet;

(d) calculating $C_2$ from $C_1$ according to the relationship $C_2=(C_1V_1)/V_2$; and (e) determining the distribution coefficient D by ascertaining the ratio of $C_1$ to $C_2$.

In another embodiment, the invention provides an acoustic method for determining a distribution coefficient D of an analyte in a mixture of two solvents, where the quantity of analyte may or may not be known, and the method comprises:

(a) combining, in a fluid reservoir, an analyte, a first volume $V_1$ of a first solvent, and a second volume $V_2$ of a second solvent that is substantially immiscible with the first solvent, thereby forming a partitioned fluid composition having an upper layer of the first solvent and a lower layer of the second solvent, wherein the analyte has a concentration $C_1$ in the first solvent and a concentration $C_2$ in the second solvent;

(b) acoustically ejecting a droplet of the upper layer;

(c) determining $C_1$ in the ejected droplet in (b);

(d) removing the upper layer from the partitioned fluid composition;

(e) acoustically ejecting a droplet of the lower layer;

(f) determining $C_2$ in the ejected droplet in (e); and (g) determining the distribution coefficient D by ascertaining the ratio of $C_1$ to $C_2$.

In a further embodiment of the invention, an acoustic system for extracting a target analyte from a sample is provided, wherein the system comprises:

(a) a fluid reservoir housing a fluid composition, wherein the fluid composition is a reaction mixture comprised of a first reactant, a second reactant, and a fluid medium, the reaction mixture having a volume in the range of about 1 nL to about 3 mL; and (b) an acoustic droplet ejector in acoustic coupling relationship with the fluid reservoir for generating acoustic radiation in a manner effective to eject a fluid droplet from the fluid composition into a droplet receiver, the ejector comprising an acoustic radiation generator and a focusing means for focusing the acoustic radiation at a focal point within the reservoir.

In an additional embodiment, the invention provides method for removing metal ions from an aqueous sample, wherein the method comprises:

adding to an aqueous sample that comprises a target analyte and a metal ion, a metal extraction composition that comprises an ionic liquid composed of (a) a positively charged crown ether, a positively charged cryptand, or a combination thereof, and (b) a negatively charged counterion;

warming the initial binary phase solution until the two phases become miscible, thereby mixing the metal ion with the metal extraction composition in a single phase solution; and cooling the single phase solution to generate a second binary phase solution comprising an upper aqueous layer and a lower layer of the metal extraction composition and the metal ion.

In a related embodiment, the invention provides a metal extraction composition for use in the aforementioned (or other) process, comprising an ionic liquid of a positively charged crown ether, a positively charged cryptand, or a combination thereof, and a negatively charged counterion.

In another embodiment, the invention provides a liquid-liquid separation method, comprising:

(a) providing, in a fluid reservoir, a fluid composition that contains a target analyte and a non-analyte component and comprises an upper layer and a lower layer, wherein (i) the target analyte is at a first analyte concentration in the upper layer and at a second analyte concentration in the lower layer, and (ii) the non-analyte component is at a first component concentration in the upper layer and at a second component concentration in the lower layer; and (b) applying focused acoustic energy to the fluid reservoir in a manner effective to eject a fluid droplet from the fluid composition into a droplet receiver.

In a further embodiment, a liquid-liquid separation method is provided that comprises:

(a) providing a sample comprising a target analyte and a non-analyte component in a first fluid;

(b) combining the sample with a second fluid to provide a fluid composition;

(c) subjecting the fluid composition to a mixing condition;

(d) allowing the fluid composition to settle into a separated fluid composition comprising an upper layer and a lower layer, wherein the target analyte has an upper analyte concentration in the upper layer and a lower analyte concentration in the lower layer, and the non-analyte component has an upper concentration in the upper layer and a lower component concentration in the lower layer, wherein either (i) the lower analyte concentration and the upper analyte concentration are different, (ii) the lower component concentration and the upper component concentration are different, or both (i) and (ii).

DETAILED DESCRIPTION OF THE INVENTION

1. Definitions and Terminology

Figure 1:
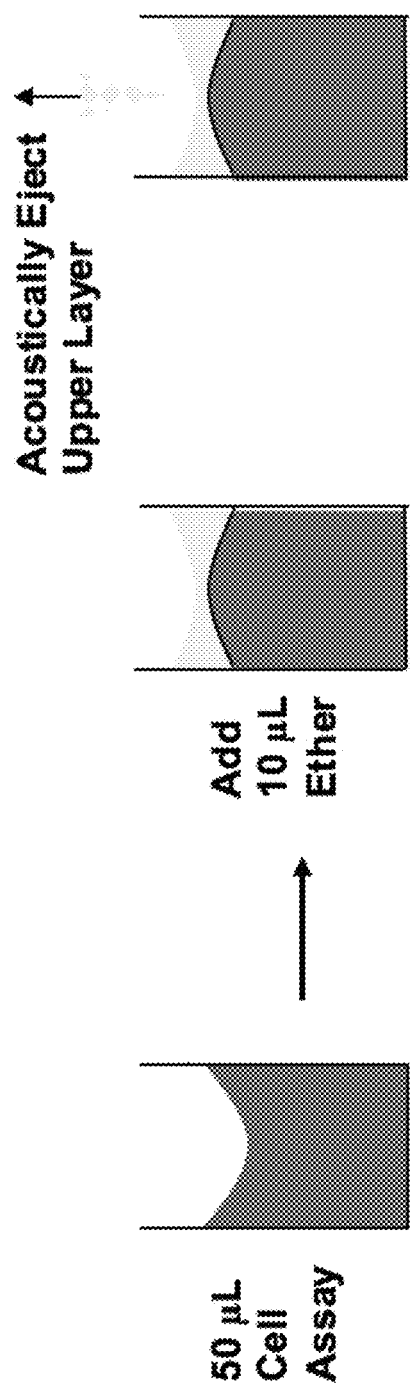
FIG. 1 schematically illustrates a representative method of the invention in which lipidic components are extracted from a biological sample into an upper organic layer, followed by acoustic ejection of the lipidic layer.

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "a fluid" refers not only to a single fluid but also to a combination of two or more different fluids that may or may not be combined, "a solvent" or "a liquid," e.g., "an ionic liquid," refers to a single solvent or liquid as well as to two or more solvents and two or more liquids, wherein the two or more solvents, or the two or more liquids, may be separate or combined.

The term "radiation" is used in its ordinary sense and refers to emission and propagation of energy in the form of a waveform disturbance traveling through a medium such that energy is transferred from one particle of the medium to another without causing any permanent displacement of the medium itself. The radiation used in conjunction with the present acoustically based extraction methods and systems is acoustic radiation.

The terms "acoustic radiation" and "acoustic energy" are used interchangeably herein and refer to the emission and propagation of energy in the form of sound waves. As with other waveforms, acoustic radiation may be focused using a focusing means, as discussed below.

The terms "focusing means" and "acoustic focusing means" refer to a means for causing acoustic waves to converge at a focal point, either by a device separate from the acoustic energy source that acts like a lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the* 1997 *IS&T NIP* 13 *International Conference on Digital Printing Technologies*, pp. 698-702.

The terms "acoustic coupling" and "acoustically coupled" used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The terms "fluid reservoir" and "reservoir," as used herein, refer to a receptacle, chamber, or surface region for holding or containing a fluid. Thus, a fluid in a reservoir necessarily has a free surface, i.e., a surface that allows a droplet to be ejected therefrom. In its one of its simplest forms, a reservoir may be a location on a solid surface that has sufficient wetting properties to hold a fluid within a localized region solely as a result of contact between the fluid and the surface, wherein the localized region serves as a reservoir.

The term "fluid," as used herein, refers to matter that is at least partially liquid. A fluid may contain a solid that is minimally, partially or fully solvated, dispersed or suspended. Examples of fluids include, without limitation, aqueous liquids (including water per se and salt water); aqueous solutions; nonaqueous liquids such as organic solvents and the like; nonaqueous solutions; colloids; suspensions; emulsions; and gels. The fluid may be a biological sample fluid in which the analyte of interest is just one component of many.

The term "moiety" as used herein refers to any particular composition of matter, e.g., a molecular fragment, an intact molecule (including a monomeric molecule, an oligomeric molecule, or a polymer), or a mixture of intact molecules or other materials (for example, a mixture of DNA of different lengths and/or sequences).

The term "near" as used herein refers to the distance from the focal point of the focused acoustic radiation to the surface of the fluid from which a droplet is to be ejected and indicates that the distance should be such that the focused acoustic radiation directed into the fluid results in droplet ejection from the fluid surface so that one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the acoustic radiation in the fluid (i.e., the acoustic radiation used to eject the droplet), more typically in the range of about 1 to about 10 times that wavelength, preferably in the range of about 1 to about 5 times that wavelength.

The term "substantially" as in, for example, the phrase "substantially identical reservoirs," refers to reservoirs that do not materially deviate in acoustic properties. For example, acoustic attenuations of "substantially identical reservoirs" deviate by not more than 10%, preferably not more than 5%, more preferably not more than 1%, and most preferably at most 0.1% from each other. Other uses of the term "substantially" involve an analogous definition.

The "target analyte" (sometimes referred to herein as simply "analyte) in the fluid sample may be any moiety that is an analyte of interest. The analyte can be an atom, an ion, a salt, a molecule, a class of molecules with a common characteristic (e.g., lipids, or salts), where the molecule and molecular class include organic compounds, inorganic compounds, and organometallic compounds. The analyte may be one that is relevant in environmental work (e.g., pertaining to water quality evaluation), in the pharmaceutical context, in the chemical industry, in the energy field, and in numerous other areas. Representative examples of analytes include, without limitation, drugs, metabolites, inhibitors, ligands, receptors, catalysts, synthetic polymers, metals, metal ions, dyes, pesticides (e.g., DDT, eldrin, tetrachlorodibenzodioxin [TCDD], etc.), carcinogens (e.g., polycyclic aromatic hydrocarbons [PCAHs]), allosteric effectors, antigens, and viruses (e.g., HIV, HPV, hepatitis A, B, C, D, E, F, or G, cytomegalovirus, Epstein-Barr virus, yellow fever, etc.). Target analytes can also be reaction products or intermediates in a multi-step reaction. In addition, target analytes can be a moiety of interest in which an extraction process of the invention involves the transfer of some fraction of the analyte from a first fluid into a second fluid. Target analytes can also be a component to be removed from a fluid, e.g., a contaminant.

Often, the analyte is a "biomolecule," also referred to herein as a "biological molecule," where those terms refer to any molecular entity that is commonly found in cells and tissues, and may be naturally occurring, recombinantly produced, biologically derived, chemically synthesized in whole or in part, or chemically or biologically modified. The term encompasses, for example, nucleic acids; amino acids; peptides, including oligopeptides, polypeptides, proteins, and conjugates thereof with non-peptide moieties, such as nucleoproteins and glycoproteins; saccharides, including monosaccharides, disaccharides, and polysaccharides; lipidic moieties; and covalent or non-covalent conjugates of any two or more of the foregoing, such as nucleoproteins, glycoproteins, lipoproteins, peptidoglycans, mucopolysaccharides, and the like. Representative examples of biomolecules include enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

"Nucleic acids" may be nucleosides or nucleotides per se, but may also comprise nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

Nucleic acids also include oligonucleotides, wherein the term "oligonucleotide," for purposes of the present invention, is generic to polydeoxyribo-nucleotides (containing 2-deoxy-D-ribose), to polyribonucleotides (containing D-ribose), to any other type of polynucleotide which is an N-glycoside of a purine or pyrimidine base, and to other polymers containing nonnucleotidic backbones. Thus, an oligonucleotide analyte herein may include oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkyl phosphoramidates and aminoalkyl phosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the terms "polynucleotide" and "oligonucleotide," and these terms are used interchangeably. These terms refer only to the primary structure of the molecule. As used herein the symbols for nucleotides and polynucleotides are according to the IUPAC-IUB Commission of Biochemical Nomenclature recommendations (Biochemistry 9:4022, 1970).

"Peptide" analytes (or "peptidic" analytes) encompass any structure comprised of one or more amino acids, and thus include peptides, dipeptides, oligopeptides, polypeptides, and proteins. The amino acids forming all or a part of a peptide analyte may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, 0-phosphoserine, N-acetylserine, N-formylmethionine, 3-methylhistidine, 5-hydroxylysine, and norleucine), and other non-conventional amino acids, as described, for example, in U.S. Pat. No. 5,679,782 to Rosenberg et al. Peptide analytes may also contain nonpeptidic backbone linkages, wherein the naturally occurring amide —CONH— linkage is replaced at one or more sites within the peptide backbone with a non-conventional linkage such as N-substituted amide, ester, thioamide, retropeptide (—NHCO—), retrothioamide (—NHCS—), sulfonamido (—SO$_2$NH—), and/or peptoid (N-substituted glycine) linkages. Accordingly, peptide analytes can include pseudopeptides and peptidomimetics. Peptide analytes can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

"Saccharides," or "saccharidic analytes," include, without limitation, monosaccharides, disaccharides, oligosaccharides, polysaccharides, mucopolysaccharides or peptidoglycans (peptido-polysaccharides), pseudopeptidoglycans, and the like, wherein monosaccharides, including monosaccharide units in disaccharides, oligosaccharides, polysaccharides, and the like, include hexoses, pentoses, and tetroses, and may be in D- or L-form, and further wherein the glycosidic linkages between monosaccharide units may be either α-glycosidic linkages or β-glycosidic linkages. Illustrative examples of saccharidic analytes include the monosaccharides fructose, glucose, dextrose, galactose, mannose, ribose, deoxyribose, allose, fucose, rhamnose, erythrose, threose, and glyceraldehyde; the disaccharides sucrose, lactose, maltose, lactulose, trehalose, cellobiose; the polysaccharides amylose, amylopectin, glycogen, cellulose, chitin, callose, laminarin, chrysolaminarin, xylan, and galactomannan; and the mucopolysaccharides (also referred to as glycosaminoglycans) chondroitin sulfate, dermatan sulfate, keratan sulfate, heparin, heparan sulfate, and hyaluronan.

"Lipids," or "lipidic analytes," refer to hydrophobic or amphiphilic molecules, and include the broad categories of fatty acids, phospholipids, glycerolipids, glycerophospholipids, sphingolipids, saccharolipids, and polyketides. Representative examples of lipidic materials include, but are not limited to, the following: phospholipids such as phosphorylated diacyl glycerides, particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof, wherein each acyl group contains about 10 to about 22 carbon atoms and is saturated or unsaturated; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group —(CO)—OH of the fatty acid is replaced with an ester moiety —(CO)—OR wherein R is a $C_1$-$C_3$ alkyl moiety optionally substituted with one or two hydroxyl groups; fatty alcohols corresponding to the aforementioned fatty acids, wherein the carboxylic acid group of the fatty acid is replaced by a —CH$_2$OH group; glycolipids such as cerebroside and gangliosides; oils, including animal oils such as cod liver oil and menhaden oil, and vegetable oils such as babassu oil, castor oil, corn oil, cottonseed oil, linseed oil, mustard oil, olive oil, palm oil, palm kernel oil, peanut oil, poppyseed oil, rapeseed oil, safflower oil, sesame oil, soybean oil, sunflower seed oil, tung oil, or wheat germ oil; and waxes, including animal waxes such as beeswax, lanolin, and shellac wax; mineral waxes such as montan wax; petroleum-derived waxes such as microcrystalline wax and paraffin wax; and plant waxes such as carnauba wax and candelilla wax.

"Extraction" and "extracting," as those terms are used herein, refers to a process that involves the migration of a target analyte from a first fluid into a second fluid and thus encompasses a separation process as explained in the previous section. The terms typically refer to the enhancement of one component of a composition, a target analyte, relative to other components of the composition, e.g., contaminants, in one of two fluidic phases. Extraction may be complete, meaning that the target analyte is completely separated from other components of a sample, so that following extraction, one fluid phase contains 100% of the target analyte. Extraction may also be partial, in which case some fraction less than 100% of the target analyte is isolated from other components in a composition. Accordingly, extraction using the present method may be for the purpose of increasing or decreasing the concentration of a target analyte in one of the fluids; removing some or all of the analyte from one of the fluids; concentrating the amount of analyte in one of the fluids; isolating the analyte; purifying the analyte; removing components, e.g., contaminants, that are initially associated with a target analyte; or a combination of two or more of the foregoing. "Liquid-liquid extraction" as the term is used herein refers to an extraction process in which the first fluid and the second fluid are independently selected from fluids that comprise liquids; as such, liquid-liquid extraction encompasses gel-liquid extraction, suspension-liquid extraction, and the like. The extraction process here is coupled with an acoustic ejection process, such that fluid droplets are acoustically ejected from a fluid having an increased or decreased concentration of a target analyte (relative to the initial concentration of target analyte in a sample or in an initial, pre-extraction fluid layer or fluid composition) or increased or decreased concentration of a non-target component (relative to the initial concentration of a non-target component in a sample or in an initial, pre-extraction fluid layer or fluid composition).

Reference to a sample "containing" or "comprising" an analyte includes both a sample known to contain an analyte, although the identity of the analyte may be unknown, and a sample suspected of containing an analyte.

The term "array" as used herein refers to a two-dimensional arrangement of features, such as an arrangement of reservoirs (e.g., wells in a well plate) or an arrangement of fluid droplets or molecular moieties on a substrate surface (as in an oligonucleotide or peptide array). Arrays are generally comprised of features regularly ordered in, for example, a rectilinear grid, parallel stripes, spirals, and the like, but non-ordered arrays may be advantageously used as well. An array differs from a pattern in that patterns do not necessarily contain regular and ordered features. In addition, arrays and patterns formed by the deposition of ejected droplets on a surface, as provided herein, are usually substantially invisible to the unaided human eye. Arrays typically, but do not necessarily, comprise at least about 4 to about 10,000,000 features, generally in the range of about 4 to about 1,000,000 features.

2. Extraction Methodology

The present invention makes use of acoustic droplet ejection (ADE) in the extraction of a target analyte from a fluid composition. In one embodiment, ADE is implemented in an extraction process to produce a fluid droplet containing a target analyte at a selected concentration. A fluid composition containing the target analyte is provided in a fluid reservoir, where the fluid composition is composed of two or more phases. That is, the fluid composition includes an upper region, or upper layer, as well as one or more lower regions, or lower layers, e.g., the fluid composition may be composed of two layers, three layers, four layers, or five or more layers. For simplicity, the method will be described with respect to a two-phase system, in which the fluid composition comprises an upper layer of a first fluid and a lower layer of a second fluid, where the first fluid and second fluid are substantially immiscible at the conditions employed for extraction. The target analyte in the fluid composition is present in the first fluid at a first concentration, and in the second fluid at a second concentration that is different from the first concentration. Generally, the first concentration and the second concentration differ by at least about 50%, e.g., at least about 85%, such as at least 50%, 55%, 60%, 65%, 70%, 75%, 80%, 85%, or more. Focused acoustic energy is applied to the fluid reservoir in a manner effective to eject a fluid droplet from the fluid composition, generally toward and into a droplet receiver. The selected concentration, i.e., the concentration of the target analyte in the ejected fluid droplet, is substantially equivalent to either the first concentration or the second concentration. In addition, the selected concentration is substantially uniform throughout the droplet. In one example, some fraction of a target analyte is moved from one fluid (e.g., a fluid containing a biological sample such as a cell lysate or the like) to a second fluid. In another example, the concentration of target analyte in two fluids may or may not change, but the components associated with the target analyte in one fluid may not be present in a second fluid after the extraction process. For instance, post-extraction, one fluid may contain target analyte and a plurality of contaminants, while a second fluid contains the target analyte without the contaminants present, or with the concentration of the contaminants substantially reduced. As another example, the extraction process involves changing the concentration of a target analyte or other component in one or more fluid layers. In a variation on the aforementioned example, extraction involves two target analytes, where the process results in an increased concentration of one of the target analytes and a decreased concentration of the other target analyte in one or more fluid layers.

As the present methodology is effective with very small sample sizes, the total fluid composition in the reservoir generally occupies a volume of no more than about 125 µL, e.g., no more than about 60 µL, no more than about 45 µL, no more than about 30 µL, and the like.

The fluid composition may comprise a sample that contains the target analyte, such as a biological sample. The biological sample may comprise a sample dissolved or suspended in a fluid, or the biological sample itself may be fluidic. Biological samples include, by way of example, tissue, tissue homogenate, cells, cell suspensions, cell extracts, whole blood, plasma, serum, saliva, sputum, nasal discharge, cerebrospinal fluid, interstitial fluid, lymph fluid, semen, vaginal fluid, or feces. More typical biological samples are comprised of tissue, cells, or blood. A biological sample may or may not be processed in some manner prior to extraction; preliminary processing methods are known in the art and include, for example, incorporation of an anticoagulant into a blood sample; separation of blood into plasma and serum; alternating centrifugation and resuspension procedures for various sample types; incorporation of a preservative or a preservative-containing transport medium into a sample; and the like. The invention is not limited in this regard, however, and is readily implemented with biological samples that have not undergone any preliminary processing as well as non-biological samples.

Target analytes in biological samples include, without limitation, proteins, peptides, peptide fragments, lipidic compounds, and nucleic acids, particularly DNA. Other biological target analytes and other types of target analytes are set forth in Part (1) of this section, "Definitions and Terminology."

Extraction of a target analyte using two or more fluids relies on the differential affinity of the analyte for one fluid relative to another fluid. The term "affinity" includes any factor or combination of factors that cause an analyte to partition into one fluid relative to another fluid. Examples of such factors include, without limitation: compatibility of analyte and fluid with respect to degree of polarity; ionic interaction between analyte and fluid; hydrogen bonding between analyte and fluid; relative hydrophilicity or hydrophobicity of analyte and solvent; and, more generally, and not unrelated to the aforementioned factors, the degree to which an analyte is soluble in a fluid.

In some embodiments, the extraction process of the invention involves use of two liquids in which the solubility of the target analyte is different, with the differential in solubilities corresponding to the differential in the first concentration and the second concentration as explained above. The differential in solubilities may be at least about 50%, e.g., at least about 85%, such as at least 50%, 55%, 60%, 65%, 70%, 75%, 80%, 85%. In some embodiments, the differential in solubilities may be less than about 50%. In other embodiments, as alluded to above, the solubility differential results from the use of a first liquid that is relatively hydrophobic and a second liquid that is relatively hydrophilic, such that a hydrophilic moiety will preferentially partition into the hydrophilic liquid, while a hydrophobic moiety will preferentially partition into the hydrophobic liquid. Such a system is useful, for instance, with a fluid composition comprising a plurality of components having different hydrophobicities, e.g., a sample containing a target analyte having a hydrophobicity that is different from the hydrophobicity of other components also present in the sample.

In other embodiments, the target analyte may be a polar molecule or salt, in which case a relatively polar solvent, which may be either protic or aprotic, is combined with a relatively non-polar solvent in the extraction process. With targets that undergo hydrogen bonding, protic solvents are useful; in such a case, a protic solvent is combined with an aprotic solvent that may or may not be nonpolar.

In addition, some analytes, including, but not limited to, some ionic analytes, can be readily extracted with ionic liquids, as will be explained infra. In some instances, an ionic liquid is used to extract an ionic analyte from another fluid composition. In other instances, an ionic liquid is used that causes an ionic analyte to preferentially partition into a second fluid composition that is not an ionic liquid. In some instances, both such processes are combined in a multistep extraction process as will be explained in further detail below.

A wide variety of solvents can be used in conjunction with the invention. In fact, virtually any solvent can be used provided that there is no adverse effect on the extraction process of the invention. Of course, nontoxic solvents are preferred. The liquids used in a single extraction step or process may vary in viscosity, volatility, and other chemical and physical characteristics. Extraction of a target analyte from a viscous material is facilitated using a relatively nonviscous fluid. When one of the solvents is volatile, concerns about evaporation can be set aside by use of a second solvent that has a lower density and is less volatile; the less volatile, lower-density solvent will form an upper layer over the lower, more volatile solvent, preventing evaporation thereof.

Solvents that can be employed in the methods and systems of the invention include aqueous and organic solvents, protic and aprotic solvents, ionic and non-ionic liquids, polymeric and nonpolymeric liquids, and the like. In combination, the fluids can form a monophasic, biphasic, triphasic, or higher multiphasic fluid composition; with a combination of two fluids, the resulting fluid composition is monophasic or biphasic. In some embodiments, the invention makes use of the degree to which the selected fluids are miscible as well as the conditions under which a combination of selected liquids can be rendered more or less miscible.

Examples of solvents useful in conjunction with the present invention include, without limitation, acetic acid, acetone, acetonitrile, ammonia, benzene, n-butanol, i-butanol, 2-butanol, t-butanol, 2-butanone, butyl acetate, t-butyl alcohol, carbon tetrachloride, chlorobenzene, chloroform, cyclohexane, cyclohexanone, cyclopentane, 1,2-dichloroethane, dichloromethane, diethyl ether, diethylene glycol, diethylene glycol dimethyl ether (diglyme), di-isopropyl ether, 1,2-dimethoxyethane (glyme, DME), dimethyl ether, dimethylformamide (DMF), dimethyl sulfoxide (DMSO), 1,4-dioxane, ethanol, ethyl acetate, ethylene glycol, ethyl formate, formic acid, furan, glycerin, heptane, hexamethylphosphoramide (HMPA), hexamethylphosphorous triamide (HMPT), n-hexane, methanol, methyl t-butyl ether (MTBE), methylene chloride, methyl ethyl ketone (MEK), methyl formate, N-methyl-pyrrolidinone (NMP), nitromethane, 1-octanol, n-pentane, petroleum ether (ligroine), piperidine, polyethylene glycol, n-propanol, i-propanol, pyridine, tetrahydrofuran (TF), toluene, trichloroethylene, triethylamine (TEA), water, deuterium oxide, o-xylene, m-xylene, p-xylene, and other solvents described in U.S. Pat. Nos. 6,548,308 and 6,642,061, both to Ellson et al., incorporated by reference herein. Preferred aqueous solvents include water, an aqueous solution of buffering compounds and/or salts, such as phosphate buffer, Tris buffer, MES buffer, HEPES buffer, ammonium bicarbonate, and the like.

Specific examples of useful solvent systems and solvent combinations herein include, without limitation: an aqueous solvent such as water or buffer solution and an organic solvent such as cyclohexane, dichloromethane, 1-octanol, n-pentane, n-butanol, or a perfluorinated or semi-fluorinated alkane solvent such as perfluoroheptane, 1,1,1,2,3,3-hexafluoropropane, pentafluoropentane, and the like; an aqueous solvent such as water or buffer solution and a lipidic solvent such as an oil; a binary system with two aqueous layers, where the aqueous liquids contain different solutes and are immiscible—see, e.g., Partitioning in Aqueous Two-Phase System: Theory, Methods, Uses, and Applications to Biotechnology, Eds. Harry Walter et al. (Academic Press, 1985); Hamta et al. (2017), "Application of polyethylene glycol based aqueous two-phase systems for extraction of heavy metals," *Journal of Molecular Liquids* 231:20-24; and Eiden et al. (2016), "Two-Phase System Rehydration of Antibody-Polymer Microarrays Enables Convenient Compartmentalized Multiplex Immunoassays," Analytical Chemistry 88(23) (also see Tavana et al. (2010) *Adv. Mater.*

Figure 2:
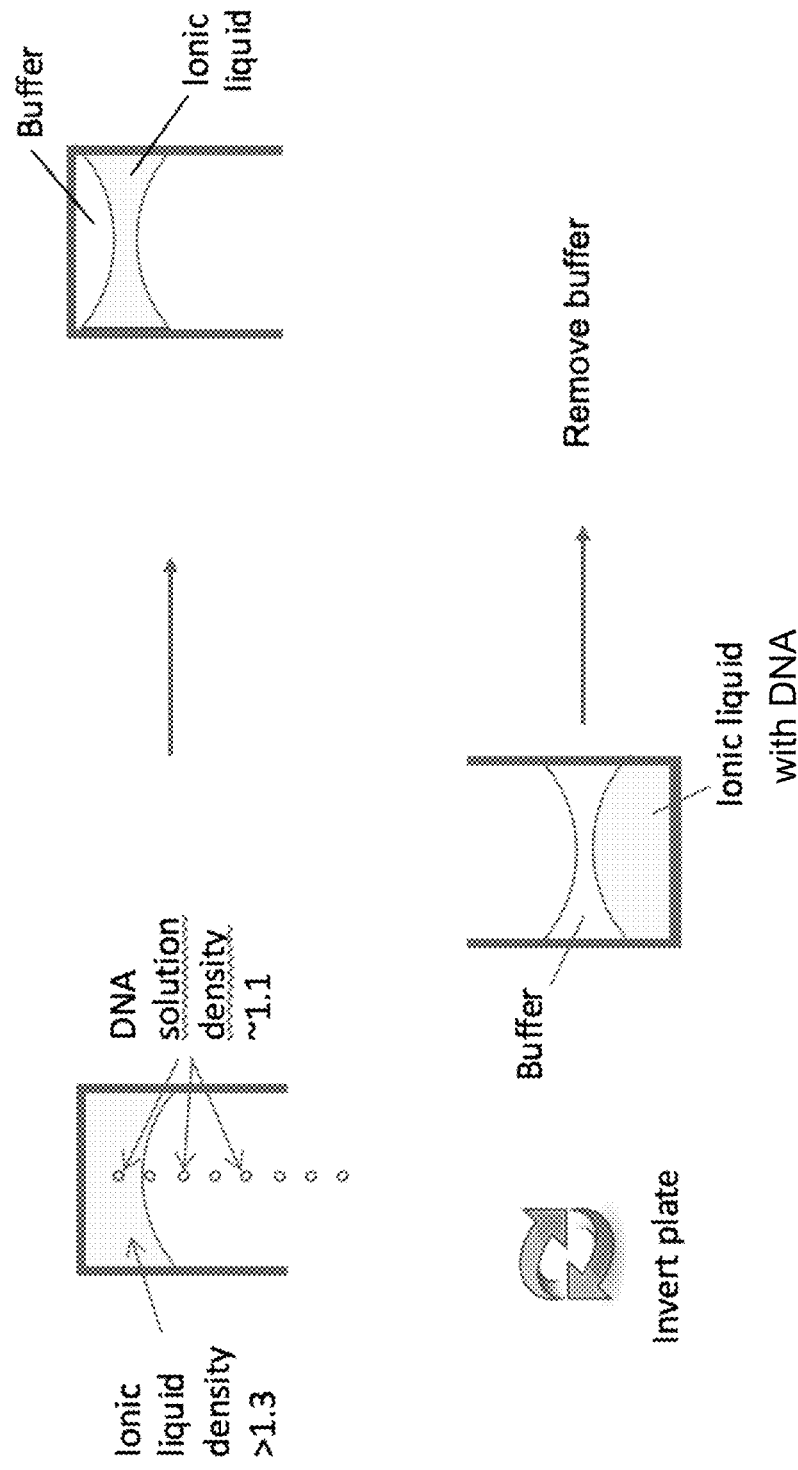
FIG. 2 and FIG. 3 schematically illustrate another representative method of the invention in which DNA is extracted from an aqueous buffer into an ionic liquid, with the buffer thereafter acoustically removed (FIG. 2) and the DNA in the ionic liquid then processed for further analysis using an extraction buffer (FIG. 3).

22(24):2628-2631 and Fang et al. (2012) *Tissue Engineering Part C: Methods* 18)9):647-657); a combination of two aqueous liquids that contain the same solute but have a different pH, as would be the case, for instance, with two aqueous liquids having the same buffer composition but where the first and second aqueous liquids are buffered to a different pH; and a binary system with two organic layers, where the organic liquids are immiscible, e.g., an ethanol/cyclohexane combination, a hexane/dichloromethane combination, an ether/chloroform combination, or the like;

The two fluids selected for the extraction process should be immiscible under the conditions employed for extraction. Miscibility, as is understood in the art, refers to the degree to which one fluid is soluble in another fluid. This solubility may vary with temperature, hydrostatic pressure, or other factors, and this variable can be advantageously incorporated into the present process. That is, the fluid composition can be subjected to a condition that induces a phase transition and renders the two fluids miscible, so that the target analyte is thoroughly mixed with both fluids. Thereafter, the fluid composition can be subjected to a condition that returns the two fluids to an immiscible state, so that acoustic energy can target a focal zone in one of the two fluid layers and eject a fluid droplet formed from and primarily comprising only one of the two layers. Miscibilities of solvents under various conditions can be determined by reference to the pertinent texts and literature, and/or can be determined empirically by combining two solvents and ascertaining the degree of miscibility at a range of temperatures, pressures, or the like. Most commonly, the miscibility of two fluids herein is altered by a change in temperature (such that raising or lowering the temperature of a fluid composition containing the two fluids alters their miscibility) and/or chemically, e.g., by addition of a salt such as sodium chloride or by a change in pH. In some cases, the two fluids employed in the present extraction processes are miscible between about 40° C. and about 90° C., It will be appreciated that the target analyte and the two fluids can be mixed prior to extraction using other techniques as well, such as repeated inversion of a container housing the analyte and fluids, stirring, sonication, agitation, moderating the temperature of the fluids, ejection (e.g., acoustic ejection) of droplets of one fluid through the other fluid (as illustrated in FIG. 2, discussed infra), and the like.

In one embodiment, the extraction method involves the use of an ionic liquid. As indicated in Part (1) of this section, an ionic liquid comprises a salt in the liquid form. That is, an ionic liquid is largely or entirely composed of ions (i.e., "substantially ionic," meaning that substantially all of the ionic liquid is ionic), in contrast to ordinary liquids, which are predominantly made up of electronically neutral species. Preferred ionic liquids for use in conjunction with the invention are purely ionic or substantially ionic, and are in a liquid state at extraction conditions. More preferred ionic liquids are "room temperature ionic liquids" (RTILs). An RTIL is composed of a salt that has a relatively low melting point and is in liquid form at temperatures below 100° C., e.g., at a temperature in the range of about 0° C. to about 100° C. RTILs are preferred herein, insofar as they offer the convenience of facilitating an extraction process that can be carried out without changing the temperature of the fluid composition. Ionic liquids are useful in the extraction of ionic analytes, e.g., negatively charged analytes such as DNA, but are useful in the extraction of other types of analytes as well. Common ionic liquids include, without limitation, imidazolium salts, pyrrolidinium salts, piperidinium salts, pyridinium salts, morpholinium salts, ammonium salts, phosphonium salts, sulfonium salts, and guanidinium salts. Suitable ionic liquids are listed in, for example, the ionic fluid catalogs published by Sigma-Aldrich (October 2012) and by EMD Chemicals Inc., and can be acquired as commercially available products. Specific examples of ionic liquids are provided below. In the following list, anion abbreviations are as follows:

Acetate ($CH_3COO^-$), OAc;
Bis[oxalato(2-)]borate, bob;
Bis(trifluoromethylsulfonyl)imide, $Tf_2N$;
Dicyanamide, DCA;
Formate ($HCO_2^-$), HCOO;
Hexafluorophosphate, $PF_6^-$;
Hydrogensulfate, $HSO_4^-$;
Hydroxyacetate ($CH_2(OH)COO^-$), HOOAc;
Methanesulfonate (mesylate), $CH_3SO_3^-$;
2-(2-Methoxyethoxy)ethyl sulfate, $CH_3(OCH_2CH_2)_2OSO_4^-$;
Methylsulfate ($CH_3-O-SO_3^-$), $MeSO_4$;
Octylsulfate ($C_8H_7SO_4^-$), $OcSO_4$;
Nitrate, $NO_3^-$;
Sulfamate, $H_2NSO_3^-$;
Tetracyanoborate, $B(CN)_4^-$;
Tetrafluoroborate, $BF_4^-$;
Thiocyanate, $SCN^-$;
p-Toluenesulfonate, or tosylate, Tos;
Tricyanomethane ($C(CN)_3^-$), TCM;
Trifluoroacetate ($CF_3COO^-$), TFA;
Trifluoromethanesulfonate (triflate, $CF_3SO_3^-$), OTf; and
Tris(pentafluoroethyl) trifluorophosphate, FAP.

Representative ionic liquids, in which it is to be understood that the first indicated species is the cation and the second indicated species is the anion (with the positive and negative signs omitted to comport with standardized ionic liquid nomenclature), include, without limitation, the following:

1-Benzyl-methylimidazolium (Zmim) salts, such as [Zmim][Cl];

N,N-Bis(2-hydroxyethyl)butylammonium (HEBA) salts, such as [HEBA][$Tf_2N$] and [HEBA][HCOO];

Bis(2-hydroxyethyl)ammonium (HEA) salts, such as [HEA][TFA] and [HEA][OAc];

Bis(2-methoxyethyl)ammonium (MEA) salts, such as MEA sulfamate;

1-Butyl-2,3-dimethylimidazolium (Bmmim) salts, such as [Bmmim][Cl], [Bmmim][I], [Bmmim][$PF_6$], [Bmmim][$BF_4$], and [Bmmim][OTf];

1-Butyl-3-methylimidazolium (Bmim) salts, such as [Bmim] [$Tf_2N$], [Bmim] [Cl], [Bmim][Br], [Bmim][I], [Bmim][DCA], [Bmim][$PF_6$], [Bmim][$HSO_4$], [Bmim][$MeSO_4$], [Bmim][$OcSO_4$], [Bmim][$BF_4$], [Bmim][$B(CN)_4$], [Bmim][Tos], [Bmim][TCM], [Bmim][TFA], [Bmim][$NO_3$], and [Bmim][OAc];

1-Butyl-3-methylpyridinium (B3mpy) salts, such as [B3mpy][Cl], [B3mpy][DCA], [B3mpy][$MeSO_4$], and [B3mpy][$BF_4$];

1-Butyl-4-methylpyridinium (B4mpy) salts, such as [B4mpy][Cl] and [B4mpy][$BF_4$];

1-Butyl-1-methylpyrrolidinium (Bmpyr) salts, such as [Bmpyr][bob], [Bmpyr][$Tf_2N$], [Bmpyr][Cl], [Bmpyr][DCA], [Bmpyr][OTf], [Bmpyr][FAP], and [Bmpyr][$B(CN)_4$];

N-Butylpyridinium chloride (Bpy) salts, such as [Bpy][Cl], [Bpy][$PF_6$], [Bpy][$BF_4$], and [Bpy][OTf];

N,N-Dimethyl(2-hydroxyethyl)ammonium (MMHEA) salts such as [MMHEA][HOOAc], [MMHEA][$Tf_2N$], and [MMIHEA][TFA];

1,3-Dimethylimidazolium (Mmim) salts, such as [Mmim][Cl], [Mmim][Br], and [Mmim][MeSO$_4$];

1,1-Dimethylpyrrolidinium (MMpyr) salts such as [MMpyr][I] and [MMpyr][Tf$_2$N];

N-Dodecyl-N,N-dimethyl-3-sulfopropylammonium Tf$_2$N and OTf;

1-(2-Ethoxyethyl)-1-methylpyrrolidinium (EOEMpyr) salts such as [EOEMpyr][Tf$_2$N], [EOEMpyr][Br], [EOEMpyr][BCN$_4$], [EOEMpyr][Tf$_2$N], and [EOEMpyr][FAP];

1-Ethyl-2,3-dimethylimidazolium (Emmim) salts such as [Emmim][Br], [Emmim][Cl], [Emmim][MeSO$_4$], and [Emmim][BF$_4$];

N-Ethyl-N,N-dimethyl-2-methoxyethylammonium Tf$_2$N, Br, B(CN)$_4$, and FAP;

N-Ethyl-N,N-dimethyl-propylammonium Tf$_2$N, Br, DCA, bis(trifluoromethylsulfonyl) imide (Nemmp tfn), bromide (Nemmp Br), dicyanamide (Nemmp DCN), B(CN)$_4$, and FAP;

1-Ethyl-3-methylimidazolium (Emim) salts such as [Emim][bob], [Emim][Tf$_2$N], [Emim][Br], [Emim][Cl], [Emim][DCA], [Emim][HSO$_4$], [Emim][MeSO$_4$], [Emim][OcSO$_4$], [Emim][B(CN)$_4$], [Emim][BF$_4$], [Emim][TFA], and [Emim][OTf];

Guanidium (gua) salts such as [gua][OTf] and [gua][FAP];

1-Hexadecyl-2,3-dimethylimidazolium (Cmmim) salts such as [Cmmim][Cl];

1-Hexadecyl-3-methylimidazolium (Cmim) salts such as [Cmim][Cl] and [Cmim][FAP];

1-Hexyl-1-methylpyrrolidinium (Hmpyr) salts such as [Hmpyr][Tf$_2$N], [Hmpyr][FAP], and [Hmpyr][Cl];

1-Hexyl-2,3-dimethylimidazolium (Hmmim) salts such as [Hmmim][Cl] and [Hmmim][FAP];

1-Hexyl-3-methylimidazolium (Hmim) salts such as [Hmim][Tf$_2$N], [Hmim][Cl], [Hmim][PF$_6$], [Hmim][BF$_4$], [Hmim][OTf], and [Hmim][FAP];

N-Hexylpyridinium (HPy) salts such as [HPy][Cl], [HPy][Tf$_2$N], [HPy][OTf], and [HPy][FAP];

1-(2-Hydroxyethyl)-3-methylimidazolium (HOE-Mim) salts such as [HOE-Mim][Tf$_2$N], [HOE-Mim][Cl], [HOE-Mim][Br], [HOE-Mim][OTf], and [HOE-Mim][FAP];

N-(3-Hydroxypropyl)pyridinium (HOP-Py) salts such as [HOP-Py][Tf$_2$N], [HOP-Py][Cl], [HOP-Py][Br], [HOP-Py][B(CN$_4$)], and [HOP-Py][FAP];

1-(3-Methoxypropyl)-1-methylpiperidinium (MOPMpi) salts such as [MOPMpi][Tf$_2$N], [MOPMpi][Cl], [MOPMpi][Br], [MOPMpi][B(CN$_4$)], and [MOPMpi][FAP];

1-Methylimidazolium (Mim) salts such as [Mim][BF$_4$];

Methyltrioctylammonium [MOc$_3$A] salts such as [MOc$_3$A][Tf$_2$N], [MOc$_3$A][TFA], and [MOc$_3$A][OTf];

1-Octyl-3-methylimidazolium (Omim) salts such as [Omim][Cl], [Omim][I], [Omim][BF$_4$], and [Omim][FAP];

1-Octyl-1-methylpyrrolidinium (OMpyr) salts such as [OMpyr][Cl];

1-Propyl-3-methylimidazolium (Pmim) salts such as [Pmim][I];

1-(3-Sulfopropyl)-3-butylimidazolium Tf$_2$N and OTf;

N-(3-sulfopropyl)-pyridinium Tf$_2$N and FAP;

Tetrabutylammonium (NB4) salts such as [NB4][Tf$_2$N];

Tetramethylammonium (Nm4) salts such as [Nm4][bob] and [Nm4][FAP];

Trihexyl(tetradecyl)phosphonium (P(h3)t) salts such as [P(h3)t][bob], [P(h3)t][Tf$_2$N], [P(h3)t][PF$_6$], [P(h3)t][BF$_4$], [P(h3)t][DCA], and [P(h3)t][FAP];

1,2,3-Trimethylimidazolium (Mmmi) salts such as [Mmmi][I];

2-Amino-1,6-dimethylimidazo[4,5-b]-pyridine salts such as 2-amino-1,6-dimethylimidazo[4,5-b]-pyridineTf$_2$N; and Triethyl-hexadecylphosphonium (THP) salts such as [THP][DCN]. Of particular interest herein are [Bmim][Tf$_2$N], [Bmim][OAc], [B3mpy][Tf$_2$N], [B4mpy][Tf$_2$N], [MOc$_3$A][Tf$_2$N], [MMpyr][Tf$_2$N], and [P(h3)t][DCA].

Polymeric ionic liquids may also be used in conjunction with the present invention. Polymeric ionic liquids are known in the art and described, for instance, in Shaplov et al. (2011), "Polymeric Ionic Liquids: Comparisons of Polycations and Polyanions," *Macromolecules* 44(24):9792-9803; Wu et al. (2017), "Polymerizable ionic liquids and polymeric ionic liquids: facile synthesis of ionic liquids containing ethylene oxide repeating unit via methanesulfonate and their electrochemical properties," *RSC Advances* 7: 5394-5401; and Mecerreyes et al. (2011), "Polymeric ionic liquids: Broadening the properties and applications of polyelectrolytes," Progress in Polymer Science 36(12): 1629-1648. Also suitable for use herein are the thermo-responsive poly(ionic liquid)-based nanogels described by Zhang et al. (2015) *Molecules* 20:17378-17392, the preparation of which is also described in that publication.

It will be appreciated that the aforementioned list of ionic liquids is merely illustrative and not intended to be limiting. Other ionic liquids useful herein include those described by Plechkova et al. (2008) *Chem. Soc. Rev.* 37:123-150; Branco et al., "Physico-Chemical Properties of Task-Specific Ionic Liquids," in *Ionic Liquids: Theory, Properties, New Approaches*, Ed. A. Korkorin (Intech, 2011); and Plechkova et al. (2015), in *Ionic Liquids Completely Uncoiled* (Wiley, 2015). Still other ionic liquids useful in conjunction with the present methods are described elsewhere in the literature and/or will be apparent to those of ordinary skill in the art. Generally preferred ionic liquids for use herein enable extraction of a significant fraction of a target analyte from a sample (on the order of 50% or more, such as 50% to 100%, 50% to 95%, 50% to 85%, 50% to 75%, etc.), and/or provide a fluid composition in which the concentration of at least one non-target component (e.g., at least one contaminant) originally associated with the target analyte is decreased in one of the fluid layers (e.g., decreased by at least 50%, such as 50% to 100%, 50% to 95%, 50% to 85%, 50% to 75%, etc.). Preferred ionic liquids are relatively non-toxic and easily used in the laboratory and have a high affinity for the fluid reservoir surface so as to concentrate an aqueous extraction fluid in the reservoir center. In some cases, it may be desirable for a selected ionic liquid to have an auditable acoustic impedance. In addition, in some instances, an ionic liquid that exhibits an extraction bias based on analyte size is preferred, while in other instances a preferred ionic liquid is one that does not exhibit an analyte size-related extraction bias (as is usually the case with nucleic acid analytes such as DNA).

In some embodiments, an ionic liquid used in the present extraction process is a magnetic ionic liquid. A magnetic ionic liquid serves as a liquid form of magnetic beads, and a magnetic ionic liquid containing the target analyte of interest can be pulled to one side of the fluid reservoir to allow easy removal of the depleted non-ionic (e.g., aqueous) layer. Magnetic ionic liquids (MILs) are known in the art and have been described in the literature. See, e.g., Clark et al. (2015) *Anal. Chem.* 87:1552-1559. As described therein, examples of MILs include benzyl trioctyl ammonium bromotrichloroferrate (III) and 1,12-di-(3-hexadecyl-benzimidazolium) dodecane bis[(trifluoromethyl)sulfonyl]imide bromotrichloroferrate (III).

In one embodiment, the method is used in the extraction of a biomolecule from a biological sample, wherein the biomolecule preferentially partitions into a first liquid relative to a second liquid, and acoustic ejection technology is used to remove one of the two phases after mixing and subsequent partitioning is complete. For instance, and as will be described in further detail infra, acoustic ejection technology can be implemented so as to rapidly and successively eject droplets of an analyte-containing upper fluid layer from a fluid reservoir, where the analyte-containing fluid droplets are ejected into a droplet reservoir for further processing and/or analysis. Acoustic ejection technology can also be implemented so as to repeatedly eject droplets of an upper fluid layer that does not contain analyte, thereby removing a non-analyte-containing upper fluid from the fluid reservoir and allowing analyte to remain in the lower fluid layer.

An example of such a method is depicted in FIG. 1. In FIG. 1, a biological sample is provided in a fluid container. The sample is a multi-component mixture in an aqueous fluid. A second fluid is added that removes at least one component from the sample by virtue of that component's preference for the second fluid. The upper layer may then be removed from the fluid container by decanting or, more preferably, by repeated acoustic ejection using, e.g., a focused acoustic ejection system as will be described infra. In the specific example illustrated in FIG. 1, it is desired to remove lipidic components from the biological sample. Accordingly, the "first fluid" is the aqueous sample itself, e.g., 50 μL of a cell assay (where the term "cell assay" is used herein to refer to a cellular sample that may or may not have been processed to some degree, such as a cell lysate), as shown in the figure, containing nucleic acids, proteins, lipids, and other components. As lipids are far more soluble in a nonpolar or low polarity solvent, the selected "second fluid" is an organic solvent such as 10 μL of diethyl ether. Following this extraction process, the lipid-containing ether layer, on top of the aqueous layer, can be removed as described above.

Interestingly, as may be seen in FIG. 1, combining two solvents with different properties in a selected fluid reservoir can result in inversion of the meniscus. That is, prior to addition of a second fluid, the first fluid has a concave meniscus, but upon addition of a second fluid the concave meniscus transforms into a convex shape at the fluid-fluid boundary. This may be desirable in multiple instances. For example, with the acoustic radiation focused at the central point in the fluid container, a lower fluid may be ejected through a central "liquid aperture" without contacting (or minimally contacting) the upper fluid layer. This allows one to omit an upper layer removal step, streamlining the overall extraction process. Meniscus reversal in this way may be accomplished by using fluid reservoirs having an interior surface that attracts or repels a particular fluid type, e.g., an organic solvent, an aqueous liquid, an ionic liquid, or the like. Fluid reservoirs with such interior surfaces can be obtained commercially, e.g., as microwell plates with different types of coatings, from numerous sources.

Another example of an extraction process of the invention will be described with respect to the extraction of a biomolecule that preferentially partitions into an ionic liquid relative to a non-ionic liquid. An important such biomolecule is DNA, which may or may not be double-stranded DNA (dsDNA). The first steps of such a method are shown schematically in FIG. 2. A biological sample may be initially processed by lysing cellular and/or tissue material therein and then resuspending the sample in a suitable aqueous buffer (e.g., Tris buffer), referred to herein as the "initial buffer." The biological sample may also comprise circulating cell-free DNA. When carried out in a microwell plate, e.g., a 384-well plate, a known quantity of an ionic liquid is added into each of a plurality of wells, as the individual wells serve as fluid reservoirs in which extraction takes place. The ionic liquid is selected so as to have a strong affinity for the DNA, and the initial buffer is selected so that the DNA preferentially partitions into the ionic liquid, i.e., relative to the buffer solution. As illustrated in FIG. 2, the method may involve adding 5 to 30 μl, e.g., 25 μl, of an ionic liquid such as [Bmim][PF$_6$] (1-butyl-3-methylimidazolium hexafluorophosphate) into the individual wells. The individual well illustrated in the figure is shown in an inverted configuration, because the well has preferably been filled with the ionic liquid by acoustically ejecting droplets upwards into the well using focused acoustic ejection technology. Alternatively, a well containing a small amount of an ionic liquid may simply be inverted, with surface tension maintaining the ionic liquid in place. The aqueous buffer containing the DNA is then introduced into each well, preferably, again, using focused acoustic droplet ejection. The volume of the two liquids may or may not be the same; in the figure, both volumes, i.e., the volume of the ionic liquid and the volume of the DNA-containing aqueous buffer, are indicated as 25 μl.

As indicated in FIG. 2, the density of the two liquids may differ. FIG. 2 provides representative and non-limiting density numbers, with the ionic liquid density indicated as being generally greater than 1.3 g/mL and the density of the aqueous DNA solution approximating 1.1 g/mL. As a result, the two liquids in the inverted fluid reservoir will partition with the aqueous buffer representing the upper layer, on the "bottom" of the well, and the ionic liquid containing the DNA below the buffer, as a lower layer. The well plate can then be inverted so that the relative positioning of the two layers switches, as shown. That is, after inversion, the ionic liquid containing the DNA is at the bottom of the well, and the aqueous buffer layer has risen through and above the ionic liquid layer.

Figure 3:
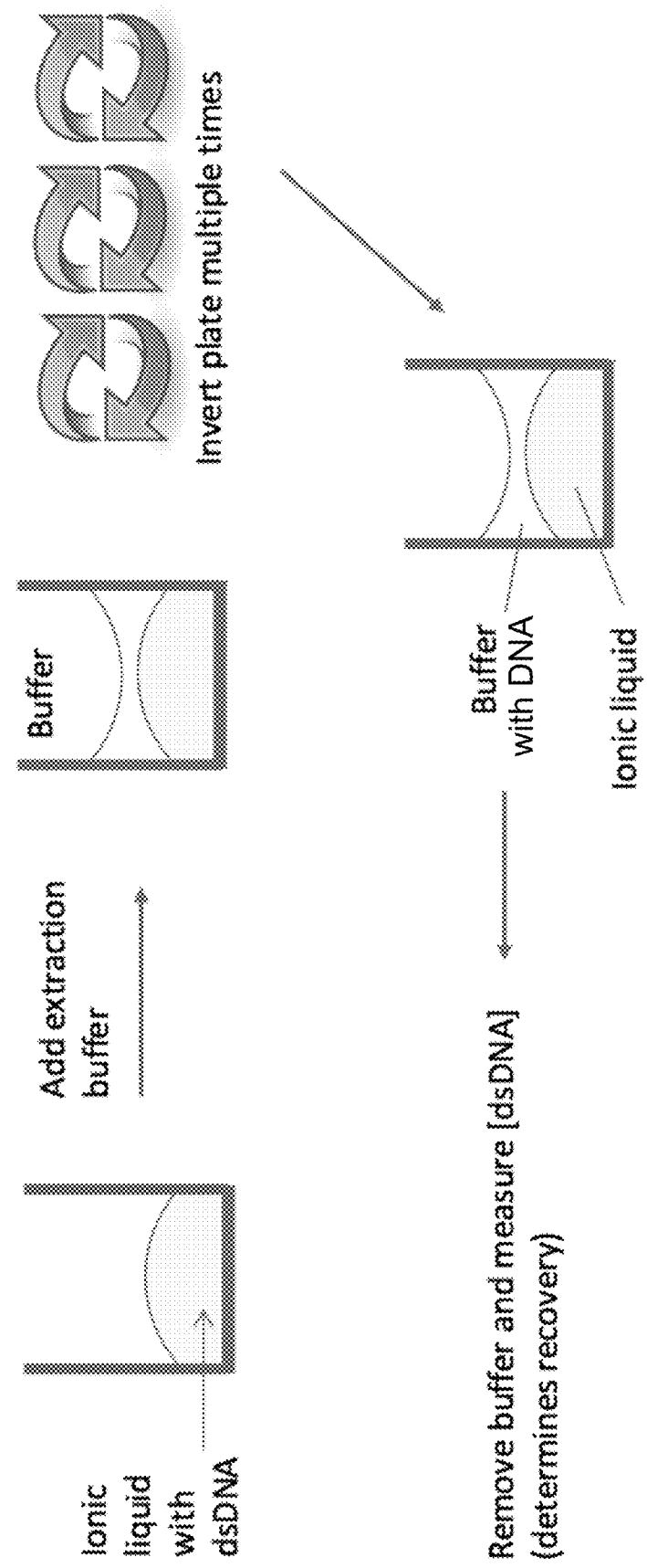

At this point, a further step is employed to remove the aqueous buffer layer. This step makes use of a second aqueous buffer solution, referred to herein as an "extraction buffer." In contrast to the initial buffer, the extraction buffer is selected so that the DNA preferentially partitions into the extraction buffer from the ionic liquid. The initial buffer and the extraction buffer may contain different buffer components, or they may contain the same buffer components but have different pH levels. The process is schematically illustrated in FIG. 3. In this case, the extraction buffer is introduced into the fluid reservoirs containing the ionic liquid with DNA therein, and the two liquids mix. As microwells in a microwell plate can be readily used as fluid reservoirs, mixing can be accomplished simply by rapidly inverting the well plate multiple times. Following mixing, and allowing time for separation of the two phases, each reservoir contains the ionic liquid as a lower layer, and the extraction buffer, with DNA therein, as an upper layer. The upper layer—i.e., the aqueous DNA layer—can be removed using any suitable means, although acoustic ejection of the layer is preferred. Using acoustic ejection, the layer may be transferred into inverted individual receptacles, as described above, or it may be acoustically ejected directly into an analytical instrument, e.g., a mass spectrometer. Transfer of the aqueous DNA solution to the analytical instrument using acoustic ejection can be carried out as described in Sinclair et al. (2016) *Journal of Laboratory Automation* 21(1):19-26 and U.S. Pat. No. 7,405,395 to Ellson et al. (Labcyte Inc., San Jose, Calif.), both of which are incorporated by reference in their entireties. Use of acoustic droplet ejection to transfer the DNA-containing aqueous liquid to an analytical instrument can be conducted with very little sample, on the order of several nanoliters, if necessary. In addition, acoustic transfer to the analytical instrument can be done very quickly, capable of generating over 10,000 data points per hour, and is therefore ideally suited to high-throughput processes.

In another embodiment, an extraction method is provided using three different fluids, wherein in a first step using a first fluid and a second fluid the target analyte partitions into the second fluid, but in a second step using the second fluid and a third fluid, the target analyte partitions into the third fluid. That is, the target analyte preferentially partitions into the second fluid when the alternative is the first fluid, but prefers the third fluid relative to the second fluid. The first, second, and third fluids are selected so as to remove multiple species, e.g., contaminants or analytes for processing separately, from the sample, thereby providing a purer solution of the target analyte in the third fluid. An example of this method is as follows: An aqueous biological sample (i.e., the first fluid, containing DNA as the target analyte) is admixed with an ionic liquid (i.e., the second fluid, into which the target analyte will partition), and allowed to partition into an upper aqueous layer and a lower ionic liquid layer. The ionic liquid is selected so that the DNA will partition into the that layer in this first step. The upper layer is then removed, preferably using acoustic ejection as described elsewhere herein, leaving a fluid composition comprising DNA, the target analyte, in the ionic liquid. In a subsequent step, the ionic liquid containing the DNA is admixed with an aqueous extraction buffer having a pH selected so that at least 60 wt. % of the DNA (and preferably at least 75 wt. %, such as at least 85 wt. %, at least 90 wt. %, at least 95 wt. %, or 100% of the DNA) will now move from the ionic liquid into the extraction buffer, which forms an upper fluid layer on top of the ionic liquid. The DNA-containing aqueous layer can then be acoustically ejected as before.

Figure 4:
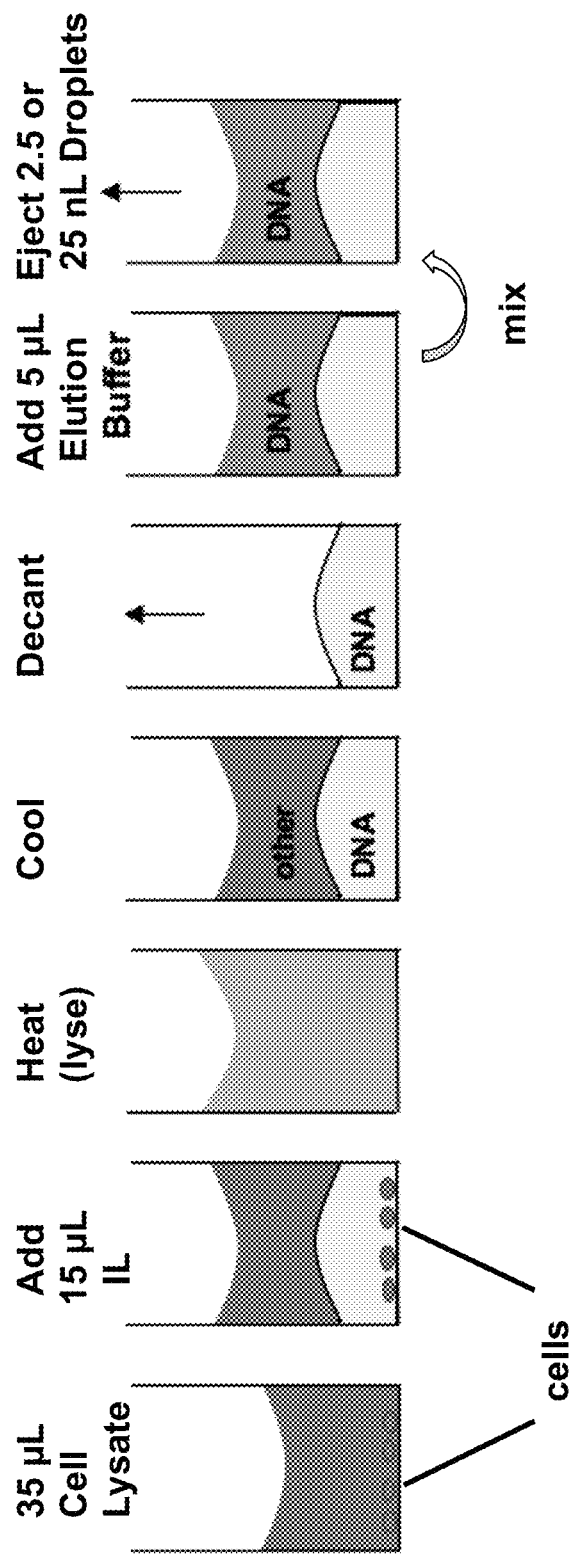
FIG. 4 schematically illustrates a method of the invention in which DNA is removed from a biological sample using an ionic liquid in a two-step extraction process.

FIG. 4 schematically illustrates the aforementioned dual extraction method using 35 μL of a biological sample (indicated as a cell lysate in the figure) containing DNA as the target analyte. The biological sample is contained in a reservoir that may be a stand-alone single reservoir, a stand-alone reservoir that is one of a group of other such reservoirs (e.g., a tube in a tube rack containing other tubes), a well in a microwell plate, e.g., a 384-well plate, or the like. The "first fluid" may be an aqueous buffer containing DNA, as indicated in the figure. An ionic liquid is added to the fluid reservoir, forming a lower layer underneath the aqueous phase. The two fluid layers are mixed using a suitable method; heating is preferred, as indicated in FIG. 4. Heating not only mixes the layers and renders them miscible (providing a suitable ionic liquid is selected that can be rendered miscible with an aqueous fluid at a relatively mild temperature), but also lyses the cells in the biological sample, releasing cell contents. The DNA will still preferentially remain in the ionic liquid, provided that the first fluid is buffered to a suitable pH, i.e., a pH at which the DNA will partition into the ionic liquid instead of remaining in the aqueous phase. The upper fluid containing unwanted cellular components is removed, by decanting, aqueous ejection, or any other suitable method; again, a preferred method involves focused acoustic ejection. After removal of the aqueous phase, a single phase of ionic liquid containing the target analyte remains in the fluid reservoir. An extraction buffer is then added and the two phases are mixed. In one embodiment, the extraction buffer, as explained above, is buffered to a pH selected so that at least 60 wt. % of the DNA (and preferably at least 75 wt. %, etc., of the DNA, as above) may move from the ionic liquid into the extraction buffer, which forms an upper aqueous base. The DNA-containing aqueous fluid layer is then acoustically ejected as before.

3. Reaction Products

As explained earlier herein, the target analyte is not limited to analytes contained in or derived from biological samples. The target analyte may be an inorganic compound, an organometallic compound, or even an atom or ion; see part (1) of this section. In a further embodiment, then, the target analyte can be a reaction product in a multi-step reaction. That is the invention additionally provides a method for the synthesis and acoustic extraction of a reaction product, where the method comprises: providing, in a fluid reservoir, a reaction mixture of a first reactant, a second reactant, and a fluid medium comprising a first liquid; subjecting the reaction mixture to a condition that causes a chemical reaction to occur between the first reactant and the second reactant to give a reaction product having a first solubility; mixing into the reaction mixture a second liquid that is immiscible with the first liquid and in which the reaction product has a second solubility that differs from the first solubility by at least 50%, thereby providing a fluid composition having an upper layer and a lower layer containing different concentrations of the reaction product; and applying focused acoustic energy to the fluid reservoir in a manner effective to eject a fluid droplet containing the reaction product into a droplet reservoir. The reaction mixture may further include a reaction catalyst, a surfactant, or additional useful components. When a reaction catalyst and/or surfactant is used, the two liquids can be selected so that the reaction product partitions into one layer and the catalyst and/or surfactant partitions into the other layer, enabling removal of these other moieties from the reaction product. In a variation on the aforementioned process, the reaction product does not necessarily partition into one of the two layers, but the other components, i.e., the catalyst and surfactant (which may be viewed as contaminants relative to the reaction product) do have an affinity for one layer relative to the other layer. The extraction process in this case thus results in the movement of the contaminants from one layer to another without concomitant movement of the target analyte, so that both layers contain target analyte but one of those layers has a much lower concentration of contaminants.

The reaction condition is generally, although not necessarily, selected from the group consisting of: allowing the reaction to proceed in the reaction mixture for a predetermined reaction time; admixing the reactants; changing the temperature of the reaction mixture; adding at least one catalyst to the reaction mixture; adding at least one surfactant to the reaction mixture; introducing at least one additional reactant into the reaction mixture; and two or more of the foregoing in combination.

In a related aspect of the invention, a method is provided for the synthesis and acoustic transfer of a reaction product. The method includes the following steps:

(a) providing, in a fluid reservoir, a reaction mixture comprised of a first reactant, a second reactant, and a fluid medium, the reaction mixture having a volume in the range of about 1 nL to about 3 mL;

(b) subjecting the reaction mixture to a reaction condition that causes a chemical reaction between the first reactant with the second reactant to give a reaction product; and (c) applying focused acoustic energy to the fluid reservoir in a manner effective to eject a fluid droplet containing the reaction product into a droplet receiver.

The reaction condition is as above, i.e., selected from the group consisting of: allowing the reaction to proceed in the reaction mixture for a predetermined reaction time; admixing the reactants; changing the temperature of the reaction mixture; adding at least one catalyst to the reaction mixture; adding at least one surfactant to the reaction mixture; introducing at least one additional reactant into the reaction mixture; and two or more of the foregoing in combination.

In a related embodiment, an acoustic system is provided for extracting a target analyte from a sample, where the system comprises: (a) a fluid reservoir housing a fluid composition, wherein the fluid composition is a reaction mixture comprised of a first reactant, a second reactant, and a fluid medium, the reaction mixture having a volume in the range of about 1 nL to about 3 mL; and (b) an acoustic droplet ejector in acoustic coupling relationship with the fluid reservoir for generating acoustic radiation in a manner effective to eject a fluid droplet from the fluid composition into a droplet receiver, the ejector comprising an acoustic radiation generator and a focusing means for focusing the acoustic radiation at a focal point within the reservoir. In one embodiment, the droplet receiver is an inverted fluid reservoir, such as a well in an inverted microwell plate. In another embodiment, the droplet receiver is an analytical instrument, such as a mass spectrometer, and the droplets ejected into the mass spectrometer—either directly or indirectly—are analyzed by the instrument.

4. Extraction of Metal Ions

In another embodiment, an extraction method is provided for removing metal ions such as alkali metal ions and alkaline earth metal ions from an aqueous sample that contains a target analyte and at least one alkali metal ion, typically lithium cations, sodium cations, or potassium cations, and/or at least one alkaline earth metal ion, such as calcium or magnesium ions. This is particularly useful in the mass spectrometry context, in which an aqueous fluid containing a target analyte of interest is transferred (e.g., via acoustic ejection) into a mass spectrometer for analysis. Ion suppression, i.e., suppression of target analyte ionization, is a well-known problem in mass spectrometry, and one of the most common causes of ion suppression is the presence of significant amounts (on the order of $10^{-5}$ M or higher) of alkali metal cations and/or alkaline earth metal cations. See Volmer et al. (2006) *LCGC North America* 24(5): 498-510. Because of their biological relevance, sodium and potassium are the two alkali metals of greatest concern. And while polyvalent cations can generally be removed from solution by precipitation to form insoluble salts (as with the precipitation of iron or copper by phosphate), monovalent alkali metal cations are more difficult to remove from solution. To date, crown ethers, although tightly binding alkali metal ions, have not been effectively used to remove alkali metals from aqueous solutions because an effective extraction process for separating the crown ether from the remainder of a sample had not yet been developed.

Accordingly, in this embodiment, a new method is provided that effectively extracts alkali metals and/or alkaline earth metals from biological samples and other aqueous compositions. The method involves adding to an aqueous sample that comprises a target analyte and an alkali metal ion and/or alkaline earth metal ion, a metal extraction composition that comprises an ionic liquid and a metal binding compound selected from crown ethers, cryptands, and combinations thereof, thereby forming an initial binary phase solution; applying a condition to the binary phase solution so that the two phases become miscible (e.g. heating), thereby mixing the metal salt with the metal extraction composition in a single phase solution; and regenerating a binary phase solution, e.g., by cooling, where the binary phase solution generated in this step comprises an upper aqueous layer and a lower layer of the metal extraction composition and the metal ion. The aqueous layer may then be ejected into a mass spectrometer (or other type of droplet receiver) for analysis of the target analyte. The metal extraction composition comprises the ionic liquid and the metal binding compound in a weight ratio in the range of about 1:100 to about 100:1, more typically in the range of about 1:10 to about 10:1.

Preferred metal binding compounds are crown ethers such as 12-crown-4, 15-crown-5, and 18-crown-6. A particularly preferred metal binding compound comprises a crown ether that has been converted to an ionic liquid by functionalization with a cationic moiety, typically, although not necessarily, with a cationic moiety that corresponds to a cation contained within the liquid salts enumerated in Part 2 of this section, "Extraction Methodology." By way of example rather than limitation, modification of a crown ether in this way can be accomplished by replacing a hydrogen atom (within a C—H group) with a functional group containing a positively charged nitrogen atom associated with a negatively charged counterion. One such crown ether salt has the structure of formula (I)

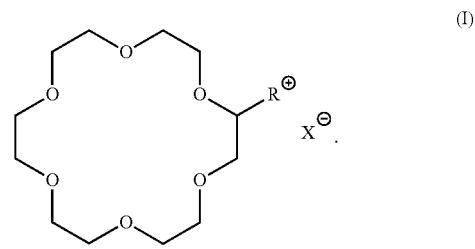

where R may be selected from tertiary amino groups and nitrogen heterocycles, and X is an anionic species such as a halide ion. A specific example of such a crown ether salt has the structure of formula (II)

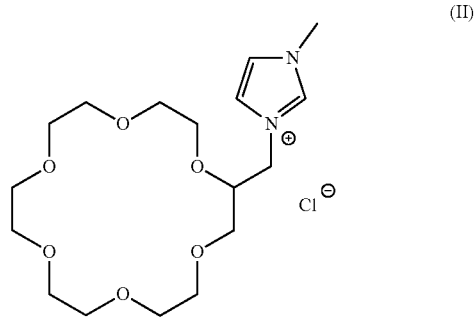 [SMILES: Cn1cc[n+](CC2COCCOCCOCCOCCOCCO2)c1 ; [Cl-]]

This crown ether salt may be synthesized from chloromethyl 18-crown-6 and N-methylimidazole using a technique analogous to that described by Dharaskar et al. (2016), "Synthesis, characterization and application of 1-butyl-3-methylimidazolium tetrafluoroborate for extractive desulfurization of liquid fuel," *Arabian Journal of Chemistry* 9:578-587.

In a related embodiment, the invention provides a metal extraction composition for use in the aforementioned extraction (or other) process, wherein the composition comprises an ionic liquid and a metal binding compound selected from crown ethers, cryptands, and combinations thereof. It should be noted that these functionalized crown ethers and cryptands can serve a dual purpose in the present extraction processes, in that they are ionic liquids with selective affinity for certain types of target analytes, as well as chelating agents for removal of alkali metal ions and alkaline earth metal ions.

5. Determination of a Distribution Coefficient of an Analyte in Two Solvents In any extraction process, including those described and claimed herein, it is extremely useful to know the distribution coefficient of a particular target analyte in two solvents. One of the solvents may be water, as in an aqueous biological sample, an aqueous buffer, or the like, and the other solvent may be a candidate solvent under consideration for use in an extraction process. Accordingly, in a further embodiment, the invention provides a method for determining a distribution coefficient D of an analyte in a mixture of two solvents, where the method comprises the following steps:

(a) combining, in a fluid reservoir, a known quantity X of an analyte with a first volume $V_1$ of a first solvent and a second volume $V_2$ of a second solvent that is substantially immiscible with the first solvent, such that the analyte has a concentration $X/(V_1+V_2)$ in the first solvent and the second solvent combined, thereby forming a partitioned fluid composition having an upper layer of the first solvent and a lower layer of the second solvent, wherein the analyte has a concentration $C_1$ in the first solvent and a concentration $C_2$ in the second solvent;

(b) acoustically ejecting a droplet of the upper layer;

(c) determining $C_1$ in the ejected droplet;

(d) calculating $C_2$ from $C_1$ according to the relationship $C_2=(C_1 V_1)/V_2$; and (e) determining the distribution coefficient D by ascertaining the ratio of $C_1$ to $C_2$.

In a related embodiment, a method is provided for determining the distribution coefficient D in two solvents, comprising:

(a) combining, in a fluid reservoir, an analyte, a first volume $V_1$ of a first solvent, and a second volume $V_2$ of a second solvent that is substantially immiscible with the first solvent, thereby forming a partitioned fluid composition having an upper layer of the first solvent and a lower layer of the second solvent, wherein the analyte has a concentration $C_1$ in the first solvent and a concentration $C_2$ in the second solvent;

(b) acoustically ejecting a droplet of the upper layer;

(c) determining $C_1$ in the ejected droplet in (b);

(d) removing the upper layer from the partitioned fluid composition;

(e) acoustically ejecting a droplet of the lower layer;

(f) determining $C_2$ in the ejected droplet in (e); and (g) determining the distribution coefficient D by ascertaining the ratio of $C_1$ to $C_2$.

6. Acoustic Ejection and High-Throughput Processes

Acoustic ejection enables rapid processing as well as generation of nanoliter-sized droplets of predetermined and consistent size; see U.S. Pat. No. 6,416,164 to Stearns et al., incorporated by reference earlier herein. The aforementioned patent describes how the size of acoustically ejected droplets from a fluid surface can be carefully controlled by varying the acoustic power, the acoustic frequency, the toneburst duration, and/or the F-number of the focusing lens, with lenses having an F-number greater than approximately 2 generally preferred. ADE thus enables ejection of "ultra-monodisperse" droplets, which in the context of the present invention means that the ejected particles have a consistent diameter, with a coefficient of variation of about 1%. This in turn enables introduction of a fluid sample in a precise and predetermined amount into the system for analysis. An additional advantage of using acoustic ejection is that droplets can be ejected from a very small sample size, on the order of 5 μl or less. This is particularly advantageous when sample availability is limited and a small fluid sample must be analyzed out of necessity. In terms of processing capability, U.S. Pat. No. 6,938,995 to Mutz et al. explains that acoustic ejection technology, used in conjunction with acoustic assessment of fluid samples in a plurality of reservoirs, can achieve analysis of over 5, 10, or even 25 reservoirs per second, translating to well in excess of 50,000 fluid samples per day.

Because of the precision that is possible using acoustic ejection technology, the present system can be used to acoustically eject sample fluid droplets of very small size. The invention is not limited in this regard, however, and the volume of acoustically ejected droplets can range from about 0.5 μL to about 3 mL. For many applications, the system of the invention is used to generate nanoliter-sized fluid droplets for analysis, where "nanoliter-sized" droplets generally contain at most about 30 nL of fluid sample, typically not more than about 10 nL, preferably not more than about 5.0 nL, more preferably not more than about 3.0 nL, such as not more than 1.0 nL, not more than about 50 μL, not more than about 25 μL, and not more than about 1 μL, including ranges of about 0.5 μL to 2.0 nL, about 0.5 μL to 1.5 nL, about 0.5 μL to 1.0 nL, about 1.0 μL to 2.0 nL, about 1.0 μL to 1.5 nL, about 1.0 μL to 1.0 nL, and the like. The typical operating range produces droplets in the range of about 1 nL to about 30 nL. Acoustic ejection of droplets from the surface of a fluid sample is carried out using an acoustic ejector as will be described in detail below. Acoustic ejection technology is particularly suited to high-throughput processing, particularly high-throughput mass spectrometry (HTMS), insofar as HTMS has been hampered by the lack of easily automated sample preparation and loading, the need to conserve sample, the need to eliminate cross contamination, the inability to go directly from a fluid reservoir into the analytical device, and the inability to generate droplets of the appropriate size.

In one embodiment, then, the system and method of the invention make use of an acoustic ejector as a fluid sample droplet generation device to eject droplets from a fluid composition in the context of liquid-liquid extraction. The acoustic ejector directs acoustic energy into a reservoir housing an analyte-containing fluid composition in a manner that causes ejection of a fluid droplet upward from the surface of the fluid.

The system may also include a means for positioning the reservoir and the acoustic ejector in acoustic coupling relationship. Typically, a single ejector is used that is composed of an acoustic radiation generator and a focusing means for focusing the acoustic radiation generated by the acoustic radiation generator. However, a plurality of ejectors may be advantageously used as well. Likewise, although a single reservoir may be used, the device typically includes a plurality of reservoirs, e.g., as an array. When the system is used to eject a droplet of an analyte-containing fluid sample from each of a plurality of reservoirs, a positioning means is incorporated in order to move a substrate containing the reservoirs (which may be positioned on a movable stage, for instance) relative to the acoustic ejector, or vice versa. Rapid and successive acoustic ejection of a fluid droplet from each of a series of reservoirs is thereby readily facilitated. Either type of positioning means, i.e., an ejector positioning means or a reservoir or reservoir substrate positioning means, can be constructed from, for example, motors, levers, pulleys, gears, a combination thereof, or other electromechanical or mechanical means.

While any acoustic droplet ejection system can be used in conjunction with present system and method, preferred ADE systems are those described in the following U.S. patents, all of common assignment herewith and incorporated by reference herein: U.S. Pat. No. 6,416,164 to Stearns et al.; U.S. Pat. No. 6,666,541 to Ellson et al.; U.S. Pat. No. 6,603,118 to Ellson et al.; U.S. Pat. No. 6,746,104 to Ellson et al.; U.S. Pat. No. 6,802,593 to Ellson et al.; U.S. Pat. No. 6,938,987 to Ellson et al.; U.S. Pat. No. 7,270,986 to Mutz et al.; U.S. Pat. No. 7,405,395 to Ellson et al.; and U.S. Pat. No. 7,439,048 to Mutz et al. Preferred ADE systems for use herein are those available from Labcyte Inc., particularly the Echo® 500-series Liquid Handler systems, including the Echo® 525, the Echo® 550, and the Echo® 555 Liquid Handlers, as well as the Echo® 600-series Liquid Handler systems, including the Echo® 600 and the Echo® 655 Liquid Handlers, all of which can eject a broad range of fluid classes with high accuracy, precision and speed.

As described in the above patents, an acoustic ejection device may be constructed to eject fluid droplets from a single reservoir or from multiple reservoirs. To provide modularity and interchangeability of components, it may sometimes be preferred for the device to be used in conjunction with a plurality of removable reservoirs, e.g., tubes in a rack or the like. Generally, the reservoirs are arranged in a pattern or an array to provide each reservoir with individual systematic addressability. In addition, while each of the reservoirs may be provided as a discrete or stand-alone container, in circumstances that require a large number of reservoirs, it is preferred that the reservoirs are contained within an integrated multiple reservoir unit. As an example, the multiple reservoir unit may be a solid surface on which discrete fluid-containing regions are maintained in place by virtue of surface wetting properties, with each localized fluid-containing region constituting a reservoir. As another example, the multiple reservoir unit may be a well plate with the individual wells serving as reservoirs. Many well plates suitable for use with the device are commercially available and may contain, for example, 96, 384, 1536, or 3456 wells per well plate, and having a full skirt, half skirt, or no skirt. Well plates or microtiter plates have become commonly used laboratory items. The Society for Laboratory Automation and Screening (SLAS) has established and maintains standards for microtiter plates in conjunction with the American National Standards Institute. The wells of such well plates are generally in the form of rectilinear arrays.

The availability of such commercially available well plates does not preclude the manufacture and use of custom-made well plates in other geometrical configurations containing at least about 10,000 wells, or as many as 100,000 to 500,000 wells, or more. Furthermore, the material used in the construction of reservoirs must be compatible with the fluid samples contained therein. Thus, if it is intended that the reservoirs or wells contain an organic solvent such as acetonitrile, polymers that dissolve or swell in acetonitrile would be unsuitable for use in forming the reservoirs or well plates. Similarly, reservoirs or wells intended to contain DMSO must be compatible with DMSO. For water-based fluids, a number of materials are suitable for the construction of reservoirs and include, but are not limited to, ceramics such as silicon oxide and aluminum oxide, metals such as stainless steel and platinum, and polymers such as polyester, polypropylene, cyclic olefin copolymers (e.g., those available commercially as Zeonex® from Nippon Zeon and Topas® from Ticona), polystyrene, and polytetrafluoroethylene. For fluids that are photosensitive, the reservoirs may be constructed from an optically opaque material that has sufficient acoustic transparency for substantially unimpaired functioning of the device.

In addition, to reduce the amount of movement and time needed to align the acoustic radiation generator with each reservoir or reservoir well during operation, it is preferable that the center of each reservoir be located not more than about 1 centimeter, more preferably not more than about 1.5 millimeters, still more preferably not more than about 1 millimeter and optimally not more than about 0.5 millimeter, from a neighboring reservoir center. These dimensions tend to limit the size of the reservoirs to a maximum volume. The reservoirs are constructed to contain typically no more than about 1 mL, preferably no more than about 100 μL, more preferably no more than about 1 μL, and optimally no more than about 1 nL, of fluid. To facilitate handling of multiple reservoirs, it is also preferred that the reservoirs be substantially acoustically indistinguishable.

The acoustic ejection device used in conjunction with the present system and method enables the acoustic ejection of droplets at a rate of at least about 250 Hz, but higher ejection rates including 500 Hz, 1 kHz, or higher are possible, with smaller droplets enabling higher repetition rates. The device is also capable of rapidly ejecting droplets from each of a plurality of reservoirs, which may be arranged in array such as is the case with a well plate or a rack of individual tubes. That is, a substrate positioning means or an ejector positioning means acoustically couples the ejector to each of a series of fluid reservoirs in rapid succession, thereby allowing fast and controlled ejection of fluid sample droplets from different reservoirs. Current commercially available technology allows for the substrate to be moved relative to the ejector, and/or for the ejector to be moved from one reservoir to another within the same substrate, with repeatable and controlled acoustic coupling at each reservoir, in less than about 0.1 second for high performance positioning means and in less than about 1 second for ordinary positioning means. As explained in U.S. Pat. No. 6,666,541 to Ellson et al., a custom designed system can reduce the reservoir-to-reservoir transition time (equivalent to the time between acoustic ejection events) to less than about 0.001 second. In order to provide a custom designed system, it is important to keep in mind that there are two basic kinds of motion: pulse and continuous. Pulse motion involves the discrete steps of moving a substrate or an ejector into position so that the ejector is acoustically coupled to a reservoir within the substrate, acoustically ejecting a droplet from a sample fluid in the reservoir, and repositioning the substrate and/or ejector so that the ejector is acoustically coupled to the next reservoir. Using a high performance positioning means with such a method allows repeatable and controlled acoustic coupling at each reservoir in less than 0.1 second. A continuous motion design, on the other hand, moves the substrate and/or ejector continuously, although not at the same speed, and provides for ejection during movement. Since the pulse width is very short, this type of process enables over 10 Hz reservoir transitions, and even over 1000 Hz reservoir transitions.

The methodology of the invention is thus ideal for implementing the disclosed extraction processes in the high-throughput context. Extraction can be carried out as described herein in each of a succession of fluid reservoirs, e.g., wells in a microwell plate, with very rapid reservoir-to-reservoir transitions and acoustic droplet ejection into any type of droplet reservoir, e.g., an inverted microwell plate or an analytical instrument.

A representative focused acoustic ejection system that can be advantageously used herein is illustrated in FIG. 1 of U.S. Pat. No. 6,666,541 to Ellson et al., the disclosure of which is incorporated by reference. As explained therein, an acoustic droplet ejection device comprises an acoustic ejector, which includes an acoustic radiation generator and a focusing means for focusing the acoustic radiation generated at a focal point within a fluid sample, near the fluid surface. The acoustic ejector is thus adapted to generate and focus acoustic radiation so as to eject a droplet of fluid from a fluid composition in a fluid reservoir. The acoustic radiation generator and the focusing means may function as a single unit controlled by a single controller, or they may be independently controlled. Any of a variety of focusing means that include curved surfaces or Fresnel lenses known in the art may be employed in conjunction with the present invention. Such focusing means are described in U.S. Pat. No. 4,308,547 to Lovelady et al. and U.S. Pat. No. 5,041,849 to Quate et al., as well as in U.S. Patent Application Publication No. 2002037579. In addition, there are a number of ways to acoustically couple the ejector to each individual reservoir and thus to the fluid therein. Although acoustic coupling can be achieved through direct contact with the fluid contained in the reservoirs, the preferred approach is to acoustically couple the ejector to the reservoirs and reservoir fluids without allowing any portion of the ejector (e.g., the focusing means) to contact any of the fluids to be ejected.

The acoustic droplet ejector may be in either direct contact or indirect contact with the external surface of each reservoir. With direct contact, in order to acoustically couple the ejector to a reservoir, it is preferred that the direct contact be wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs that have a specially formed inverse surface.

Optimally, acoustic coupling is achieved between the ejector and each of the reservoirs through indirect contact, provided by an acoustic coupling medium placed between the ejector and the base of the fluid reservoir. The acoustic coupling medium may be an acoustic coupling fluid, preferably an acoustically homogeneous material in conformal contact with both the acoustic focusing means and the underside of the reservoir. The system may contain a single acoustic ejector or it may contain multiple ejectors. Single ejector designs are generally preferred over multiple ejector designs because accuracy of droplet placement and consistency in droplet size and velocity are more easily achieved with a single ejector. However, the invention is not limited to single ejector designs.

When more than one fluid reservoir is used in the present methods, the reservoirs are preferably both substantially identical and substantially acoustically indistinguishable, although identical construction is not a requirement. As explained earlier in this section, the reservoirs may be separate removable components in a tray, rack, or other such structure, but they may also be fixed within a plate, e.g., a microwell plate, or other substrate. Each reservoir is preferably substantially axially symmetric, as shown, having vertical walls extending upward from circular reservoir bases, although other reservoir shapes and reservoir base shapes may be used. The material and thickness of each reservoir base should be such that acoustic radiation may be transmitted therethrough and into the fluid sample contained within each reservoir.

In operation, a fluid reservoir is filled with a fluid composition that comprises a sample containing a target analyte, as explained previously. The target analyte is generally in extracted form, in a solvent or solvent mixture, or it may be in lower fluid layer as explained earlier herein. The acoustic ejector is positioned just below the fluid reservoir, with acoustic coupling between the ejector and the reservoir provided. Once the ejector and reservoir are properly positioned with respect to each other, the acoustic radiation generator is activated to produce acoustic radiation that is directed by the focusing means to a focal point near a fluid surface within the reservoir (where a fluid surface may represent either a liquid-air interface or a liquid-liquid interface. As a result, a fluid droplet is ejected from the fluid surface toward a droplet receiver such as a substrate, an inverted reservoir, a well in an inverted microwell plate, a droplet transport device, or an analytical instrument. In a multiple-reservoir system, e.g., a multiwell plate or tube rack, can then be repositioned relative to the acoustic ejector such that another reservoir is brought into alignment with the ejector and a droplet of the next fluid composition can be ejected.

An analytical instrument into which the ejected droplet may be directed can be any instrument used for detecting a target analyte, determining the amount or concentration of target analyte in a sample, or determining the chemical composition of a target analyte. When the analytical instrument is a mass spectrometer or other type of device requiring the analyte to be in ionized form, the exiting droplets pass through an ionization region, prior to entering the mass spectrometer or other analytical instrument requiring that analyte be in ionized form. In the ionization region, a selected ionization source, e.g., an electrospray ion source, converts the analyte to ionized form. With ejected fluid droplets that contain the target analyte in ionized form, exposure to an ionization source is unnecessary; see, e.g., Provisional U.S. Patent Application Ser. No. 62/590,079 for "System and Method for the Acoustic Loading of an Analytical Instrument Using a Continuous Flow Sampling Probe" to Datwani et al., filed Nov. 22, 2017, the disclosure of which is incorporated by reference herein. Exemplary analytical instruments include, but are not limited to, mass spectrometers, spectroscopy devices, separation systems, and combinations thereof. Exemplary ionization techniques include, but are not limited to, chemical ionization, electron impact ionization, desorption chemical ionization, inductively coupled plasma ionization, and atmospheric pressure ionization, including electrospray ionization and atmospheric pressure chemical ionization, and atmospheric pressure photo-ionization. Exemplary separation methods include, but are not limited to liquid chromatography, solid phase extraction, HPLC, capillary electrophoresis, or any other liquid phase sample cleanup or separation process. Exemplary mass spectrometers include, but are not limited to, sector mass spectrometers, time-of-flight mass spectrometers, quadrupole mass filter mass spectrometers, three-dimensional quadrupole ion trap mass spectrometers, linear quadrupole ion trap mass spectrometers, toroidal ion trap mass spectrometers, and Fourier transform ion cyclotron resonance mass spectrometers.

In addition, the invention herein encompasses modifications of the acoustic ejection process to optimize results, as previously described. For example, as explained in U.S. Pat. No. 6,932,097 to Ellson et al., U.S. Pat. No. 6,938,995 to Ellson et al., U.S. Pat. No. 7,354,141 to Ellson et al., U.S. Pat. No. 7,899,645 to Qureshi et al., U.S. Pat. No. 7,900,505 to Ellson et al., U.S. Pat. No. 8,107,319 to Stearns et al., U.S. Pat. No. 8,453,507 to Ellson et al., and U.S. Pat. No. 8,503,266 to Stearns et al., the above acoustic droplet ejectors can be utilized for characterization of a fluid composition in a reservoir, e.g., to measure the height of the fluid meniscus as well as other properties, such as fluid volume, viscosity, density, surface tension, composition, acoustic impedance, acoustic attenuation, speed of sound in the fluid, etc., any or all of which can then be used to determine optimum parameters for droplet ejection, including acoustic power, acoustic frequency, toneburst duration, and/or the F-number of the focusing lens. As another example, acoustic interrogation processes can be used to optimize the relative position of the acoustic ejector and a fluid-containing reservoir in a focus-activated acoustic ejection system, as described in U.S. Pat. Nos. 8,544,976 and 8,882,226 to Ellson et al. An additional example is a method for optimizing the amplitude of the acoustic radiation used to eject fluid droplets, by analyzing the waveforms of acoustic radiation reflected from surfaces within the reservoir prior to ejection; see U.S. Pat. Nos. 7,717,544 and 8,770,691 to Stearns et al. Droplet size and consistency can be ensured using the method of U.S. Pat. No. 6,383,115 to Hadimioglu et al., and variations in reservoir properties can be controlled for using the methods of U.S. Pat. No. 7,481,511 to Mutz et al. and U.S. Pat. No. 7,784,331 to Ellson et al.

7. Dynamic Tracking of a Liquid-Liquid Boundary

In a preferred embodiment, a combination of the aforementioned methods and systems for optimizing acoustic ejection processes can be advantageously used in the present context. More specifically, the vertical position of the boundary between two fluid layers in a fluid reservoir can be tracked before each acoustic ejection event, as can the height of the entire fluid composition in the reservoir. This can be done using the acoustic interrogation techniques described in the aforementioned patents. During an extraction process of the invention, then, the height of the upper fluid (i.e., the distance from the liquid-liquid boundary to the meniscus, at the center point) can be calculated from the combination of the overall (central) height of the fluid composition and the vertical location of the (center of) the liquid boundary; that is, the height of the upper fluid equals the overall fluid height minus the height of the identified boundary. This, in turn, facilitates a process in which acoustic ejection can be stopped after complete ejection of an upper layer without also ejecting a lower layer.

It is to be understood that while the invention has been described in conjunction with a number of specific embodiments, the foregoing description as well as the examples that follow are intended to illustrate and not limit the scope of the invention. In this regard, no attempt is made to show structural details of the invention in more detail than is necessary for the fundamental understanding of the invention, the description taken with the drawings and/or examples making apparent to those skilled in the art how the invention may be embodied in practice. This disclosure includes all modifications and equivalents of the subject matter recited in the claims appended hereto as permitted by applicable law. Moreover, any combination of the elements of the invention described herein are encompassed by the disclosure unless otherwise indicated herein or clearly contradicted by context.

All patents, patent publications, literature references, and other materials cited herein are incorporated by reference in their entireties.

EXPERIMENTAL

An Echo® 555 Liquid Handler (Labcyte Inc., San Jose, Calif.) serves as the acoustic droplet ejector (ADE) system, as the system can eject a broad range of fluid classes with high accuracy, precision and speed. Fluid samples are loaded into wells of a 384-well polypropylene source plate and the source plate mounted to a motorized stage system to provide for automated sampling from any source well. The Echo 555 system is calibrated for aqueous solutions, including methanol up to 50% in water as well as up to 50% acetonitrile. The acoustic transducer of the system can also be utilized for auto-characterization of a fluid in a reservoir, to measure the height of the fluid meniscus as well as other properties (e.g., fluid volume, viscosity, density, surface tension, acoustic impedance, acoustic attenuation, speed of sound in the fluid, etc.) to determine optimum parameters for droplet ejection, including acoustic power, the acoustic frequency, the toneburst duration, and/or the F-number of the focusing lens.

The fluid reservoirs were wells in 384-well microplates. Added to the fluid reservoirs, i.e., to the sample-loaded wells of the microwell plate, are a suitable biocompatible buffer, e.g., 20 μL Tris/EDTA buffer and 20 μL BMIM $PF_6$ as the ionic liquid. Some wells are coated with a hydrophilic, amine coating, and others are not; surfactant is added into some wells, but not others. An extraction/separation protocol of the invention is followed, with fluid droplets injected into an inverted microwell plate or into an analytical instrument such as amass spectrometer.

The invention claimed is:

1. A method for extracting a target analyte from a fluid sample, comprising:
 (a) adding the fluid sample to an ionic liquid selected so that the target analyte preferentially partitions from the fluid sample into the ionic liquid and dissolves therein, thereby providing a first mixture with a first layer comprising a solution of the target analyte in the ionic liquid and a second layer deriving from the fluid sample;
 (b) removing the second layer from the first mixture;

(c) combining the solution of the target analyte in the ionic liquid with an extraction solvent effective to facilitate preferential partitioning of the target analyte from the ionic liquid into the extraction fluid, thereby providing a second mixture with a third layer comprising the ionic liquid and a fourth layer comprising a solution of the target analyte in the extraction fluid; and (d) directing a first focused acoustic energy toward the second mixture so as to eject one or more droplets from the third layer or one or more droplets from the fourth layer.

2. The method of claim 1, wherein the target analyte is ionic.

3. The method of claim 2, wherein the target analyte comprises a nucleic acid.

4. The method of claim 3, wherein the fluid sample is an aqueous sample.

5. The method of claim 4, wherein the extraction fluid is not an ionic liquid.

6. The method of claim 5, wherein the extraction fluid comprises an aqueous buffer.

7. The method of claim 1, wherein the second layer is above the first layer, and wherein the second layer is removed from the first mixture using focused acoustic droplet ejection.

8. The method of claim 1, wherein the fourth layer is above the third layer, and wherein the first focused acoustic energy is applied to the fourth layer so as to eject the one or more droplets from the fourth layer toward a droplet receiver.

9. The method of claim 1, wherein the fourth layer is beneath the third layer, and wherein the first focused acoustic energy is applied to the fourth layer so as to eject the one or more droplets from the fourth layer toward a droplet receiver.

10. The method of claim 1, wherein the fourth layer is beneath the third layer, and wherein the first focused acoustic energy is applied to the third layer so as to remove the third layer from the second mixture.

11. The method of claim 10, further comprising, subsequent to removing the third layer, applying a second focused acoustic energy to the fourth layer so as to eject the one or more droplets from the fourth layer toward a droplet receiver.

12. The method of claim 11, wherein removing the third layer comprises removing an amount of the third layer sufficient to create a liquid aperture in the third layer to facilitate ejection of the one or more droplets from the fourth layer.

13. The method of claim 1, wherein the analyte has a first solubility in the ionic liquid and a second solubility in the extraction fluid, and further wherein the second solubility is at least 85% greater than the first solubility.

14. The method of claim 1, wherein the ionic liquid and the extraction fluid have different hydrophobicities.

15. The method of claim 1, wherein the ionic liquid comprises a salt that is in liquid form at a temperature in the range of about 0° C. to about 100° C.

16. The method of claim 1, wherein the ionic liquid comprises an imidazolium salt, a pyrrolidinium salt, a piperidinium salt, a pyridinium salt, a morpholinium salt, an ammonium salt, a phosphonium salt, a sulfonium salt, or a guanidinium salt.

17. The method of claim 1, wherein the ionic liquid comprises a salt selected from:
1-benzyl-methylimidazolium (Zmim) salts;
N,N-bis(2-hydroxyethyl)butylammonium (HEBA) salts;
bis(2-hydroxyethyl)ammonium (HEA) salts;
bis(2-methoxyethyl)ammonium (MEA) salts;
1-butyl-2,3-dimethylimidazolium (Bmmim) salts;
1-butyl-3-methylimidazolium (Bmim) salts;
1-butyl-3-methylpyridinium (B3mpy) salts;
1-butyl-4-methylpyridinium (B4mpy) salts;
1-butyl-1-methylpyrrolidinium (Bmpyr) salts;
N-butylpyridinium chloride (Bpy) salts;
N,N-dimethyl(2-hydroxyethyl)ammonium (MMHEA) salts;
1,3-dimethylimidazolium (Mmim) salts;
1,1-dimethylpyrrolidinium (MMpyr) salts;
N-dodecyl-N,N-dimethyl-3-sulfopropylammonium salts;
1-(2-ethoxyethyl)-1-methylpyrrolidinium (EOEMpyr) salts;
1-ethyl-2,3-dimethylimidazolium (Emmim) salts;
N-ethyl-N,N-dimethyl-2-methoxyethylammonium (NemmEA) salts;
N-ethyl-N,N-dimethyl-propylammonium (Nemmp) salts;
1-ethyl-3-methylimidazolium (Emim) salts;
guanidium salts;
1-hexadecyl-2,3-dimethylimidazolium (Cmmim) salts;
1-hexadecyl-3-methylimidazolium (Cmim) salts;
1-hexyl-1-methylpyrrolidinium (Hmpyr) salts;
1-hexyl-2,3-dimethylimidazolium (Hmmim) salts;
1-Hexyl-3-methylimidazolium (Hmim) salts;
N-hexylpyridinium (HPy) salts;
1-(2-hydroxyethyl)-3-methylimidazolium (HOE-Mim) salts;
N-(3-hydroxypropyl)pyridinium (HOP-Py) salts;
1-(3-methoxypropyl)-1-methylpiperidinium (MOPMpi) salts;
1-methylimidazolium (Mim) salts;
methyltrioctylammonium [MOc3A] salts;
1-octyl-3-methylimidazolium (Omim) salts;
1-octyl-1-methylpyrrolidinium (OMpyr) salts;
1-propyl-3-methylimidazolium (Pmim) salts;
1-(3-sulfopropyl)-3-butylimidazolium salts;
N-(3-sulfopropyl)-pyridinium salts;
tetrabutylammonium (NB4) salts;
tetramethylammonium (Nm4) salts;
trihexyl(tetradecyl)phosphonium (P(h3)t) salts
1,2,3-trimethylimidazolium (Mmmi) salts such as [Mmmi][I];
2-amino-1,6-dimethylimidazo[4,5-b]-pyridine salts; and
triethyl-hexadecylphosphonium (THP) salts.

18. The method of claim 17, wherein the salt comprises an anion selected from halide, acetate, bis(trifluoromethylsulfonyl)imide, formate, trifluoroacetate, bis[oxalato(2-)]borate; bis(trifluoromethylsulfonyl)imide, dicyanamide, hexafluorophosphate, hydrogensulfate, hydroxyacetate, methanesulfonate, 2-(2-methoxyethoxy)ethyl sulfate, methylsulfate, octylsulfate, nitrate, sulfamate, tetracyanoborate, tetrafluoroborate, thiocyanate, p-toluenesulfonate, tricyanomethane, trifluoroacetate, trifluoromethanesulfonate, and tris(pentafluoroethyl) trifluorophosphate.

19. A method for extracting a target analyte from a fluid sample, comprising:
(a) adding the fluid sample to an ionic liquid selected so that the target analyte preferentially partitions from the fluid sample into the ionic liquid and dissolves therein, thereby providing a first mixture with a first layer comprising a solution of the target analyte in the ionic liquid and a second layer deriving from the fluid sample;

(b) removing the second layer from the first mixture by applying focused acoustic energy to the second layer so as to eject one or more droplets from the second layer; and (c) combining the solution of the target analyte in the ionic liquid with an extraction fluid effective to facilitate preferential partitioning of the target analyte from the ionic liquid into the extraction fluid, thereby providing a second mixture with a third layer comprising the ionic liquid and a fourth layer comprising a solution of the target analyte in the extraction fluid.

20. An acoustic fluid ejection system for extracting a target analyte from a fluid sample, comprising:

an acoustic radiation generator to generate and direct acoustic radiation; and a reservoir for containing a fluid, wherein the reservoir is configured to be acoustically coupleable to the acoustic radiation generator so that activation of the acoustic radiation generator directs acoustic radiation into the reservoir;

wherein the acoustic fluid ejection system is configured to:

accept, within the reservoir, the fluid sample and an ionic liquid selected so that the target analyte preferentially partitions from the fluid sample into the ionic liquid and dissolves therein, thereby providing a first mixture with a first layer comprising a solution of the target analyte in the ionic liquid and a second layer deriving from the fluid sample;

direct, by the acoustic radiation generator, a first acoustic radiation at the second layer so as to cause a plurality of droplets to be ejected from the second layer so as to remove the second layer;

accept, within the reservoir, a extraction fluid effective to facilitate partitioning of the target analyte from the ionic liquid into the extraction fluid, thereby providing a second mixture with a third layer comprising the ionic liquid and a fourth layer comprising a solution of the target analyte in the extraction fluid; and direct, by the acoustic radiation generator, a second acoustic radiation at the fourth layer so as to cause a plurality of droplets to be ejected from the fourth layer toward a droplet receiver.

21. The acoustic fluid ejection system of claim 20, wherein the droplet receiver comprises a microplate or a tube.

22. The acoustic fluid ejection system of claim 20, wherein the fourth layer is above the third layer.

23. The acoustic fluid ejection system of claim 20, wherein the fourth layer is beneath the third layer.

24. The acoustic fluid ejection system of claim 20, wherein the target analyte comprises a nucleic acid.

25. The acoustic fluid ejection system of claim 20, wherein the ionic liquid comprises an imidazolium salt, a pyrrolidinium salt, a piperidinium salt, a pyridinium salt, a morpholinium salt, an ammonium salt, a phosphonium salt, a sulfonium salt, or a guanidinium salt.

\* \* \* \* \*